(12) United States Patent
Taketomi et al.

(10) Patent No.: US 11,647,964 B2
(45) Date of Patent: May 16, 2023

(54) REMOTE WATCHING SYSTEM AND REMOTE WATCHING APPLICATION

(71) Applicant: PARAMOUNT BED CO., LTD., Tokyo (JP)

(72) Inventors: Takumi Taketomi, Tokyo (JP); Masato Shimokawa, Tokyo (JP); Sota Nishiura, Tokyo (JP); Yuka Kobayashi, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 29 days.

(21) Appl. No.: 17/324,262

(22) Filed: May 19, 2021

(65) Prior Publication Data

US 2022/0142588 A1 May 12, 2022

(30) Foreign Application Priority Data

Nov. 10, 2020 (JP) .............................. JP2020-187157

(51) Int. Cl.
| | |
|---|---|
| *A61B 5/00* | (2006.01) |
| *G08B 5/38* | (2006.01) |
| *A47C 21/00* | (2006.01) |
| *A61B 5/024* | (2006.01) |
| *A61B 5/08* | (2006.01) |
| *A61B 5/11* | (2006.01) |
| *A61B 5/0205* | (2006.01) |

(52) U.S. Cl.
CPC ............ *A61B 5/742* (2013.01); *A47C 21/003* (2013.01); *A61B 5/024* (2013.01); *A61B 5/0205* (2013.01); *A61B 5/0816* (2013.01); *A61B 5/11* (2013.01); *A61B 5/6892* (2013.01); *G08B 5/38* (2013.01)

(58) Field of Classification Search
CPC ....... A61B 5/742; A61B 5/0205; A61B 5/024; A61B 5/0816; A61B 5/11; A61B 5/6892; A47C 21/003; G08B 5/38; G08B 21/0461
See application file for complete search history.

(56) References Cited

U.S. PATENT DOCUMENTS

| | | | | |
|---|---|---|---|---|
| 8,810,392 | B1 * | 8/2014 | Teller | G08B 21/24 340/572.1 |
| 2007/0157385 | A1 * | 7/2007 | Lemire | A61G 7/08 5/618 |
| 2014/0225746 | A1 * | 8/2014 | Nagase | A61B 5/746 340/870.09 |
| 2016/0128468 | A1 * | 5/2016 | Lafleche | A47B 23/025 5/2.1 |

(Continued)

FOREIGN PATENT DOCUMENTS

| | | | | |
|---|---|---|---|---|
| CN | 105049511 | * | 7/2015 | ............ G08C 17/02 |
| JP | 2020-129396 A | | 8/2020 | |

*Primary Examiner* — Hongmin Fan
(74) *Attorney, Agent, or Firm* — Birch, Stewart, Kolasch & Birch, LLP

(57) ABSTRACT

A remote watching system includes a sensor attached to a bed apparatus and configured to acquire biological information about a bed user who uses the bed apparatus, a server configured to receive the biological information from the sensor and output a notification that is based on the biological information, and a mobile terminal configured to receive the notification and display the received notification, wherein the server outputs only a previously set notification or the mobile terminal displays only a previously set notification.

13 Claims, 19 Drawing Sheets

(56) References Cited

U.S. PATENT DOCUMENTS

| | | | |
|---|---|---|---|
| 2016/0140307 A1* | 5/2016 | Brosnan | G06Q 10/10 600/509 |
| 2017/0330430 A1* | 11/2017 | Goodfield | A61G 7/05 |
| 2018/0035955 A1* | 2/2018 | Mayoras, Jr. | A61B 5/6892 |
| 2018/0206798 A1* | 7/2018 | Murai | G16H 15/00 |
| 2019/0307405 A1 | 10/2019 | Terry et al. | |
| 2019/0336085 A1 | 11/2019 | Kayser et al. | |
| 2020/0066415 A1 | 2/2020 | Hettig et al. | |
| 2021/0338111 A1* | 11/2021 | Onishi | H01L 41/1132 |

* cited by examiner

FIG. 8

REMOTE WATCHING SYSTEM AND REMOTE WATCHING APPLICATION

CROSS-REFERENCE TO RELATED APPLICATIONS

This application is based upon and claims the benefit of priority from the prior Japanese Patent Application No. 2020-187157, filed on Nov. 10, 2020; the entire contents of which are incorporated herein by reference.

FIELD

Embodiments relate to a remote watching system and a remote watching application.

BACKGROUND

In recent years, as the decreasing birthrate and aging population and the nuclearization of family progress, there have been increasing cases where an aged person lives apart from his or her son or daughter. Moreover, there have also been increasing cases where, even in the case of living together, a son or daughter works at a working place distant from his or her home and only an aged person stays home during the day. In such cases, a system capable of appropriately caring for a person requiring support, such as an aged person, with a small burden is being demanded.

BRIEF DESCRIPTION OF THE DRAWINGS

FIGS. 3A, 3B, and 3C are diagrams illustrating the bed apparatus for use in the embodiment, in which FIG. 3A illustrates a lowered-bed horizontal state, FIG. 3B illustrates a heightened-bed back-raising state, and FIG. 3C illustrates a sloped-bed state.

FIG. 8 is a screen diagram illustrating a setting screen of the mobile terminal.

DETAILED DESCRIPTION

Figure 1:
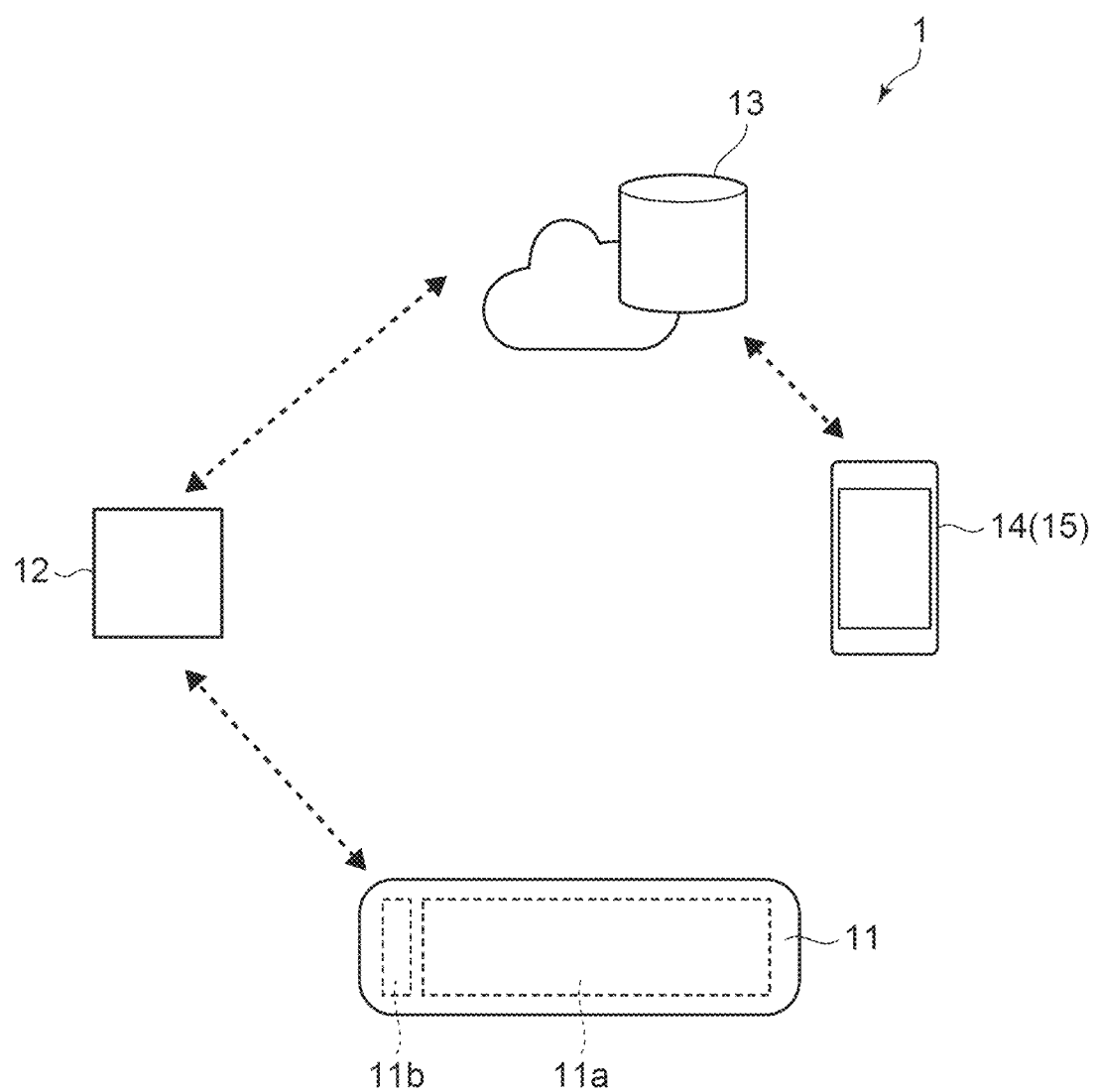
FIG. 1 is a diagram illustrating a remote watching system according to an embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, or a combination of hardware and software in execution.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software stored on a non-transitory electronic memory or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer-readable (or machine-readable) device or computer-readable (or machine-readable) storage/communications media having a computer program stored thereon. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

In general, one aspect of the present application is directed to providing a remote watching system and a remote watching application each of which is capable of appropriately caring for a person requiring support with a small burden.

According to one embodiment, a remote watching system includes a sensor attached to a bed apparatus and configured to acquire biological information about a bed user who uses the bed apparatus, a server configured to receive the biological information from the sensor and output a notification that is based on the biological information, and a mobile terminal configured to receive the notification and display the received notification, wherein the server outputs only a previously set notification or the mobile terminal displays only a previously set notification.

According to one embodiment, a remote watching application is installed on a mobile terminal capable of communicating with a server, the remote watching application receiving, from the server, a notification that is based on biological information about a bed user who uses a bed apparatus and issued from a sensor capable of communicating with the server and attached to the bed apparatus, and causing the mobile terminal to display a previously set notification.

According to embodiments, a remote watching system and a remote watching application each of which is capable of appropriately caring for a person requiring support with a small burden can be implemented.

In the following description, embodiments are described with reference to the drawings.

FIG. 1 is a diagram illustrating a remote watching system according to an embodiment.

Figure 2:
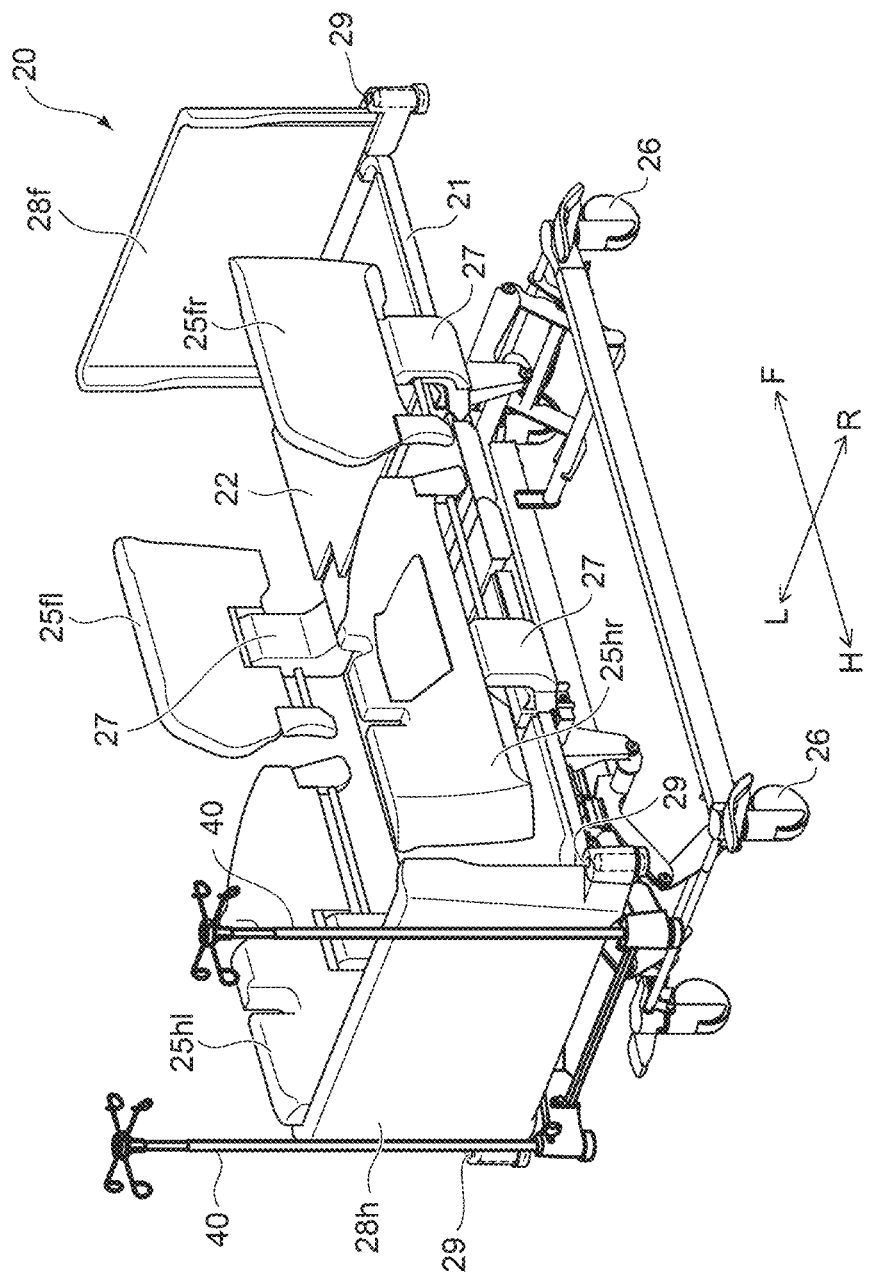
FIG. 2 is a perspective view illustrating a bed apparatus for use in the embodiment.

FIG. 2 is a perspective view illustrating a bed apparatus for use in the embodiment.

Figure 3A:
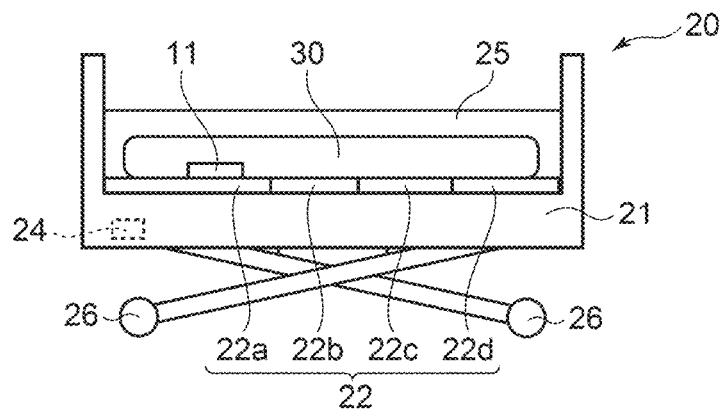
Figure 3B:
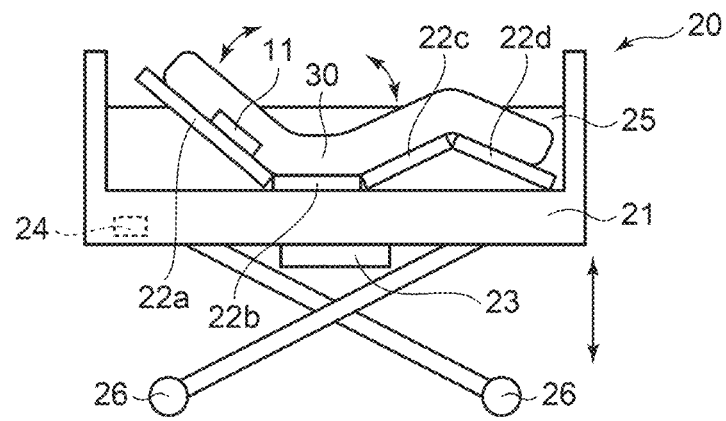
Figure 3C:
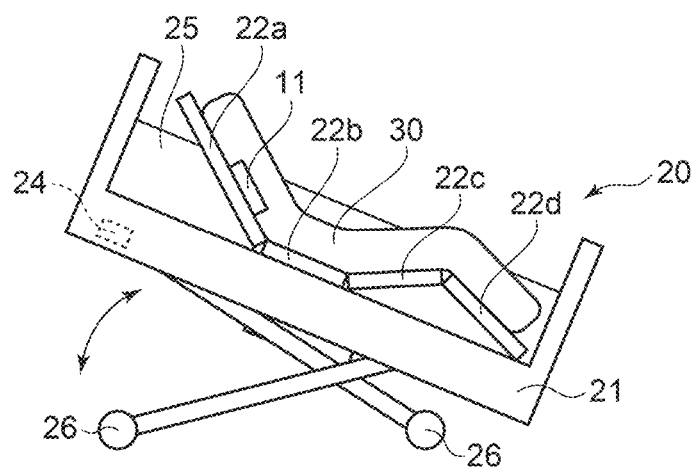

FIGS. 3A, 3B, and 3C are diagrams illustrating the bed apparatus for use in the embodiment, in which FIG. 3A illustrates a lowered-bed horizontal state, FIG. 3B illustrates a heightened-bed back-raising state, and FIG. 3C illustrates a sloped-bed state.

As illustrated in FIG. 1, a remote watching system 1 according to the present embodiment includes a sensor 11, a router 12, a server 13, and a mobile terminal 14. The mobile terminal 14 has a remote watching application 15 according to the present embodiment installed thereon.

Moreover, the remote watching system 1 can further include a non-contact thermometer and a camera. The non-contact thermometer and the camera can be placed near the sensor 11 and can be configured to input and output signals to and from the sensor 11. Additionally, the remote watching system 1 can further include a watching robot and a robot. The watching robot is equipped with a microphone and a loudspeaker and gives a reaction using voice. The robot is equipped with a movable portion and is able to move and perform a predetermined operation. The watching robot and the robot are placed near the sensor 11 and are controllable by the sensor 11.

The sensor 11 is attached to a bed apparatus 20 to be used. As illustrated in FIG. 2, the bed apparatus 20 can be used, for example, as a care bed in a care environment (including a medical care environment). The bed apparatus 20 is not limited to a care bed, and can be a general bed or a bed for intensive care unit (ICU).

In FIG. 2, arrow H indicates a direction pointing toward a head side H taken when a bed user lies on the bed apparatus 20. Arrow F indicates a direction pointing toward a foot side F taken when the bed user lies on the bed apparatus 20. Arrow R indicates a direction pointing toward a right side R taken when the bed user lies face-up on the bed apparatus 20. Arrow L indicates a direction pointing toward a left side L taken when the bed user lies face-up on the bed apparatus 20. The head side H and the foot side F are also collectively referred to as a "longitudinal direction". The right side R and the left side L are also collectively referred to as a "lateral direction". Each of the longitudinal direction and the lateral direction is the horizontal direction or a direction close to the horizontal direction. The longitudinal direction and the lateral direction are perpendicular to each other.

As illustrated in FIG. 2 and FIGS. 3A to 3C, the bed apparatus 20 includes a frame 21, a bottom 22 provided on the frame 21, an actuator 23, which controls the height and angle of the frame 21 and the angle of the bottom 22, a controller 24, which controls the actuator 23, side rails 25 attached to the frame 21, and casters 26 attached to lower portions of the frame 21 in such a way as to be rotatable. The bottom 22 includes, for example, a back section 22a, a seat section 22b, an upper leg section 22c, and a lower leg section 22d. A mattress 30 is placed on the bottom 22, and the bed user (not illustrated) lies on the mattress 30. The mattress 30 can be an urethane mattress or an air mattress. The air mattress includes an air mattress for a Gatch bed in which a plurality of air cells is juxtaposed in the bed longitudinal direction. The bed user is, for example, a person requiring care, who receives nursing care, or a person requiring support, who is not a person requiring care but requires support in daily life, for example, an aged person.

The side rails 25 includes, in a side extending in the longitudinal direction on the right side R of the frame 21, a head-side right side rail 25hr arranged on the head side H and a foot-side right side rail 25fr arranged on the foot side F and, in a side extending in the longitudinal direction on the left side L of the frame 21, a head-side left side rail 25hl arranged on the head side H and a foot-side left side rail 25fl arranged on the foot side F. The head-side right side rail 25hr, the foot-side right side rail 25fr, the head-side left side rail 25hl, and the foot-side left side rail 25fl are also collectively referred to as "side rails 25". Each side rail 25 is provided with a lock unit 27. There are a case where the side rails 25 are constantly coupled to the frame 21 and a case where the side rails 25 are attachable to and detachable from the frame 21.

In a case where the side rails 25 are constantly coupled to the frame 21, the side rails 25 take two states including a state in which the side rails 25 are moved down, i.e., a storage state in which major portions of the side rails 25 are situated on the lower side of the frame 21, and a state in which the side rails 25 are moved up, i.e., a usage state in which major portions of the side rails 25 are situated on the upper side of the frame 21.

In a case where the side rails 25 are in the storage state, the lock unit 27 is in an unlocked state. In a case where the side rails 25 are moved up to transition from the storage state to the usage state, the lock unit 27 automatically enters into a locked state, and the side rails 25 are held while being situated on the upper side of the frame 21. Ina case of causing the side rails 25 to transition from the usage state to the storage state, an operation of unlocking the lock unit 27 to bring the lock unit 27 into the unlocked state and then moving down the side rails 25 to bring the side rails 25 into the storage state.

In a case where the side rails 25 are attachable to and detachable from the frame 21, the side rails 25 take two states including a storage state in which the side rails 25 are removed from the frame 21 and are then stored in a different place and a usage state in which the side rails 25 are attached to the frame 21. The side rails 25 can be provided with the lock unit 27 or can be provided with no lock unit.

In a case where the side rails 25 are provided with the lock unit 27, when the side rails 25 are in the storage state, the lock unit 27 is in the unlocked state. In a case where the side rails 25 have been attached to the frame 21, the lock unit 27 can automatically enter into the locked state or can be manually brought into the locked state. The side rails 25 can be foldable.

The bed apparatus 20 can be provided with a head board 28h at the head side H of the frame 21 and can be provided with a foot board 28f at the foot side F of the frame 21. Moreover, the bed apparatus 20 can be provided with pole holders 29, for example, at corner portions of the frame 21. Each pole holder 29 allows a pole 40 to be attached thereto as needed. Depending on physical conditions of the bed user, as the pole 40, an intravenous drip pole (IV pole) can be attached or a pole used to hold an oxygen tank or another medical device can be attached.

The controller 24 is able to switch between the unlocked state and locked state of the lock unit 27 of each side rail 25. Moreover, the controller 24 is able to switch between an unlocked state in which each caster 26 is allowed to rotate and a locked state in which each caster 26 is prevented from rotating. Additionally, the controller 24 is able to output, by wire or by wireless, one or more types of information, for example, all of the pieces of information, selected from a group including information about the height and angle of the frame 21, information about the angle of the bottom 22, the presence or absence of the side rails 25, information about the usage state and the storage state, information about the locked state of the lock unit 27, information about the locked state of the casters 26, information about the presence or absence of attachment and the locked state of the head board 28h and the foot board 28f, and information about the internal pressure of each air cell of the air mattress.

Additionally, the controller 24 is able to output, by wire or by wireless, information about equipment present near the bed apparatus 20. The information about equipment includes, for example, information about an excretion detection sensor and information about a wandering detection sensor. Moreover, the controller 24 is able to output, by wire or by wireless, information obtainable from provided home electrical appliances, for example, information about the usage condition of an electric water boiler, information about turning on and off of devices, such as an air conditioner, a television set, a radio, and a personal computer, and information about the usage conditions of such devices. Additionally, the controller 24 is able to output, by wire or by wireless, information about the environment, for example, information about the temperature, humidity, illuminance, and odor in a room furnished with the bed apparatus 20.

The controller 24 can be operated via a user interface device (a hand-held remote switch) connected to the bed apparatus 20 or can be operated via the mobile terminal 14. The user interface device can include a light emitter. The light emitter is able to perform turning-on, blinking, and turning-out of light in response to control provided by the controller. Moreover, the user interface device can include a liquid crystal screen. The liquid crystal screen can display the above-mentioned information output by wire or by wireless from the controller 24 or can display information input from the mobile terminal 14.

FIG. 3A illustrates a lowered-bed horizontal state, in which the frame 21 is in a lowered position and all of the sections of the bottom 22 are horizontal. This state is suitable for a case where, for example, the bed user sleeps. In a case where the side rails 25 are provided, it is desirable that the side rails 25 be in the usage condition and the lock unit 27 be in the locked state.

FIG. 3B illustrates a heightened-bed back-raising state, in which the frame 21 is in a heightened position and the back section 22a, the upper leg section 22c, and the lower leg section 22d are sloped. This state is suitable for a case where, for example, the bed user is wakening on the bed apparatus 20.

FIG. 3C illustrates a sloped-bed state, in which the frame 21 is sloped and the back section 22a, the upper leg section 22c, and the lower leg section 22d are sloped. This state brings the bed user close to a sitting position and is, therefore, suitable for a case where the bed user acts for, for example, reading, eating, or talking.

In addition to these, if the frame 21 is heightened and the bottom 22 is made horizontal, the bed apparatus 20 enters into a state suitable for a case where a caretaker cares for the bed user. Moreover, if the frame 21 is heightened and the back section 22a is sloped, the bed apparatus 20 enters into a state suitable for a case where the bed user stands up at the bedside.

The shape of the sensor 11 is sheet-like. The sensor 11 is located between the back section 22a and the mattress 30. The sensor 11 is provided with a pressure measurement unit 11a and a control circuit 11b. The pressure measurement unit 11a measures a pressure via the mattress 30. The control circuit 11b records and analyzes a temporal change of the pressure measured by the pressure measurement unit 11a.

This enables the control circuit 11b to detect the heartbeat rate, respiratory rate, and body motion of the bed user via the mattress 30 and thus determine whether the bed user is in a sleeping state or in a wakeful state. Moreover, this enables the control circuit 11b to record and analyze a temporal change of a load measured by the pressure measurement unit 11a and thus determine whether the bed user is present on the bed apparatus 20 (whether the bed user is in bed) or is away from the bed apparatus 20 (whether the bed user is out of bed).

Furthermore, the pressure measurement unit 11a can be provided with a plurality of units and be capable of detecting a pressure for each unit. This enables knowing the position of the bed user on the bed apparatus 20. For example, in a case where the pressure measurement unit 11a is provided with two units and such two units are arranged along the lateral direction of the bed apparatus 20, it can be known that the bed user is lying while being close to the right side of the bed apparatus 20. Moreover, the sensor 11 can be provided within the actuator 23. In this case, the pressure measurement unit 11a of the sensor 11 measures a load put on the actuator 23. The sensor 11 is able to measure the body weight of the bed user based on a load put on the actuator 23. The sensor 11 can be a load cell. The load cell is provided, for example, at each of four corner portions of the frame 21. In this case, the load cells are able to be used to measure the body weight of the bed user. In a case where the mattress 30 is an air mattress, an internal pressure of each air cell mounted in the air mattress is able to be used to measure a load.

Moreover, the control circuit 11b is provided with a communication unit and thus outputs, by wireless or by wire, biological information about the measured heartbeat rate, respiratory rate, and body motion of the bed user and information about a result of determination as to whether the bed user is in a sleeping state or in a wakeful state. The control circuit 11b outputs information using, for example, a wireless local area network (wireless LAN) such as Wi-Fi®. Moreover, the control circuit 11b acquires bed information about the bed apparatus 20 from the controller 24 of the bed apparatus 20, and performs various types of determinations based on the biological information and the bed information. Specific examples of the determinations are described below. Then, the control circuit 11b also outputs results of these determinations.

The sensor 11 and the router 12 are arranged within the same building, for example, within the same room. The sensor 11 and the router 12 are able to communicate with each other via, for example, Wi-Fi©. The router 12 is able to access a communication network such as the Internet.

The server 13 is built out on, for example, a cloud. The router 12 and the server 13 are able to communicate with each other via a communication network such as the Internet. The server 13 performs processing described below based on information transmitted from the router 12, and, as needed, performs communication with the mobile terminal 14 via a communication network such as the Internet.

The mobile terminal 14 is, for example, a smartphone. Furthermore, the mobile terminal 14 can be, for example, a tablet or a notebook personal computer, or can be a dedicated receiver. As mentioned above, the mobile terminal 14 has the remote watching application 15 installed thereon. A user of the mobile terminal 14 (hereinafter referred to as a "terminal user") is a person who watches over the bed user and, as needed, cars for the bed user, and is, for example, a family member of the bed user. The terminal user can live with the bed user or can live apart from the bed user. The terminal user living apart from the bed user can be living nearby or living distantly. Furthermore, the term "living nearby" means that the terminal user resides at a place from which the terminal user is able to visit the residence of the bed user as needed, and the term "living distantly" means that the terminal user resides at a place from which the terminal user is unable to visit the residence of the bed user.

The remote watching application 15 is able to display options of messages which the terminal user inputs on the screen of the mobile terminal 14 and set input buttons for given options. The options of messages include, for example, "I have seen the notification", "Please lock the casters", "I'll come there now", and "I can't come there for you and, therefore, has requested an available person to visit you". This message is displayed on the liquid crystal screen of the user interface device of the bed apparatus 20, and is visible by the bed user. Moreover, the controller 24 can display, in addition to the above-mentioned messages input by the terminal user, for example, messages such as "(Your daughter) has viewed the notification", "I'll lock the casters", "I have locked the casters", "A caretaker will visit you", and "A person next door will visit you" on the liquid crystal screen of the user interface device of the bed apparatus 20.

The server 13 can be configured to be able to output commands for controlling the bed apparatus 20 to the controller 24 according to the bed information. Moreover, the terminal user can be allowed to operate the bed apparatus 20 via the mobile terminal 14. This enables the terminal user to cause the bed apparatus 20 to operate remotely from a notification destination using the Internet of Things (IoT). The controller 24 can, based on commands issued by the server 13 or the terminal user, lock the casters 26 of the bed apparatus 20, move down the frame 21, move up the side rails 25, or, when the bottom 22 operates, display a forenotice message such as "The bottom will operate now", on the liquid crystal screen of the user interface device of the bed apparatus 20 and then move the bottom 22.

Next, operations of the remote watching system and the remote watching application according to the present embodiment are described.

Each of the remote watching system and the remote watching application according to the present embodiment notifies the terminal user of information about the bed user. The information about the bed user includes the above-mentioned biological information acquired from the sensor 11, the above-mentioned bed information acquired from the bed apparatus 20, and other pieces of information acquired from various devices such as a clinical thermometer and a camera. While various notifications are conceivable as the notification to the terminal user, in the following description, a notification indicating that the bed user is currently in a dangerous condition, a notification indicating that the bed user is currently out of bed or in bed, and a notification indicating that the heartbeat rate and respiratory rate of the bed user have changed are used as examples for description. However, other types of notifications can be used.

First, notification of a dangerous condition is described.

Figure 4:
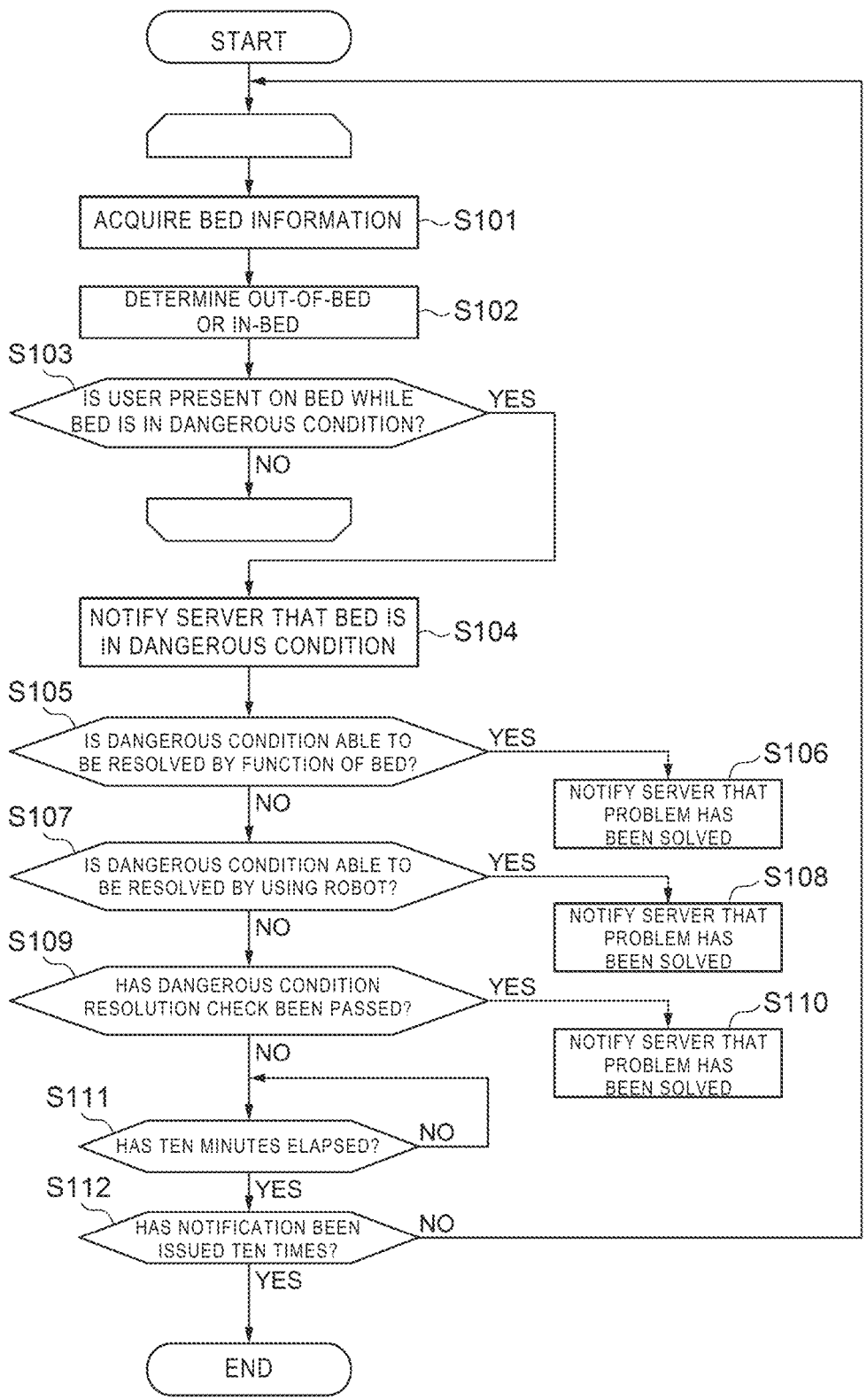
FIG. 4 is a flowchart illustrating an operation of a sensor in notification of a dangerous condition.

FIG. 4 is a flowchart illustrating an operation of the sensor in notification of a dangerous condition.

Figure 5:
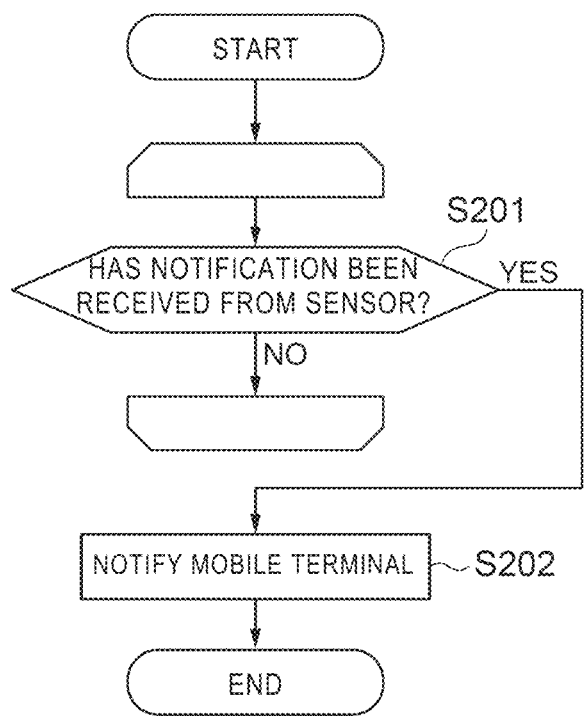
FIG. 5 is a flowchart illustrating an operation of a server in notification of a dangerous condition.

FIG. 5 is a flowchart illustrating an operation of the server in notification of a dangerous condition.

Figure 6:
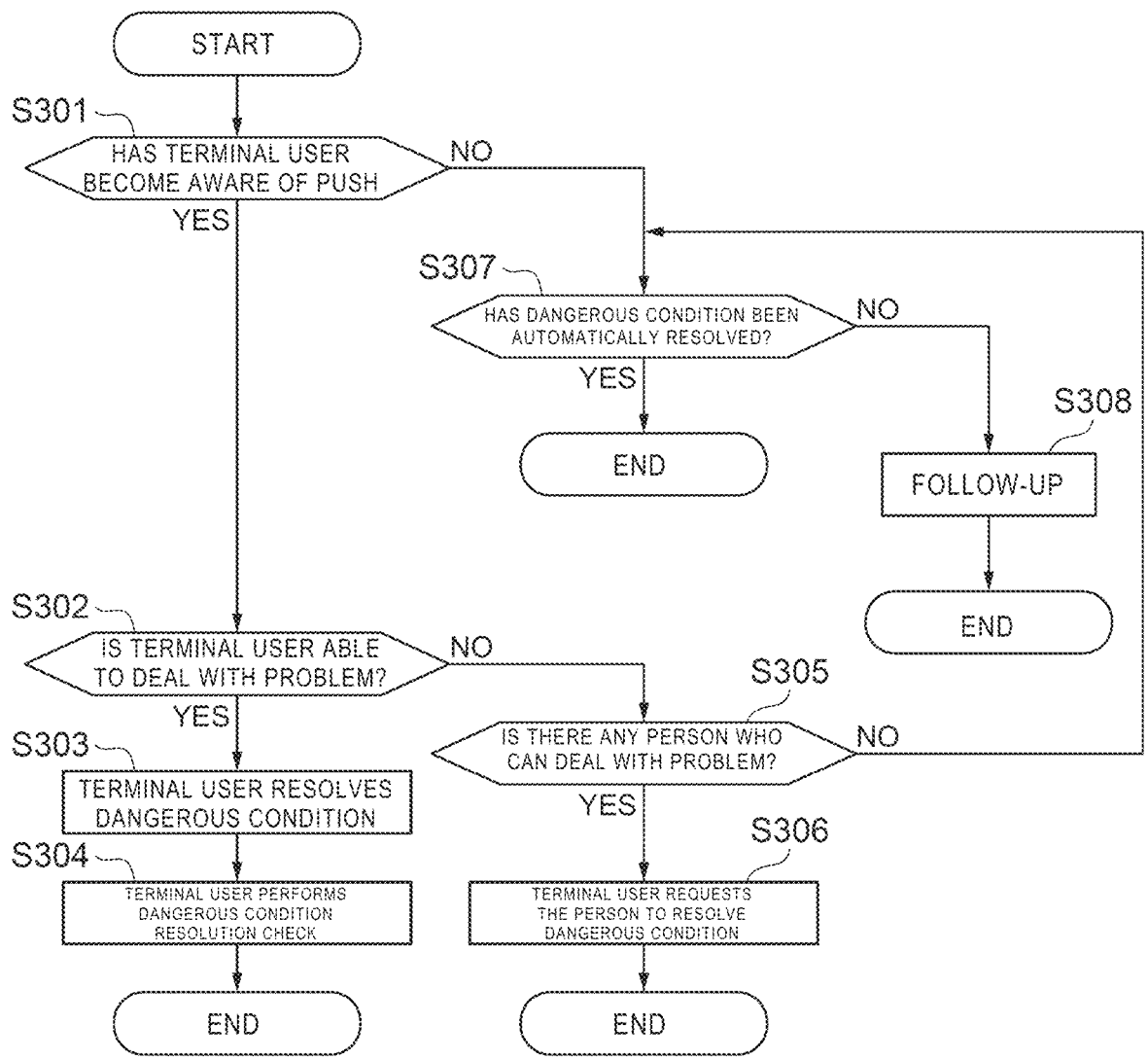
FIG. 6 is a flowchart illustrating an action of a terminal user in notification of a dangerous condition.

FIG. 6 is a flowchart illustrating an action of the terminal user in notification of a dangerous condition.

FIGS. 7A, 7B, 7C, and 7D are screen diagrams illustrating screens which the remote watching application according to the present embodiment displays on the mobile terminal.

Furthermore, in the screen diagrams illustrated in FIGS. 7A to 7D, a region used for only display is surrounded by a dashed line, and a region not only used for display but also allowing an operation by touch is surrounded by a solid line. The same also applies to the other screen diagrams described below.

First, an operation of the control circuit 11*b* of the sensor 11 is described.

First, in step S101 illustrated in FIG. 4, the control circuit 11*b* of the sensor 11 acquires bed information about the bed apparatus 20 from the controller 24 of the bed apparatus 20. For example, the control circuit 11*b* acquires, from the controller 24, information about the height and angle of the frame 21, the angle of each section of the bottom 22, whether each side rail 25 is in the storage state or in the usage state, the locked state of the lock unit 27, and the locked state of the casters 26.

Next, in step S102, the control circuit 11*b* performs out-of-bed and in-bed determination based on biological information about the bed user. Specifically, when having detected the heartbeat rate, respiratory rate, or body motion of the bed user based on a result of measurement by the pressure measurement unit 11*a*, the control circuit 11*b* determines that the bed user is present on the bed apparatus 20, i.e., the bed user is in bed, and, when having detected none of the heartbeat rate, respiratory rate, and body motion of the bed user, the control circuit 11*b* determines that the bed user is not present on the bed apparatus 20, i.e., the bed user is out of bed.

Next, in step S103, the control circuit 11*b* determines, based on results obtained in steps S101 and S102, whether the bed user is present on the bed apparatus 20 with the bed apparatus 20 being in a dangerous condition. The bed apparatus 20 being in a dangerous condition represents, for example, a case where the frame 21 is too heightened, a case where the side rails 25 are in the storage state, a case where the side rails 25 are in the usage state and the lock unit 27 is in the unlocked state, or a case where the casters 26 are in the unlocked state. Then, if determining that the bed apparatus 20 is not in a dangerous condition or the bed user is out of bed, the control circuit 11*b* sets the determination result to "NO" and then repeats steps S101 to S103. On the other hand, if determining that the bed apparatus 20 is in a dangerous condition and the bed user is in bed, the control circuit 11*b* sets the determination result to "YES" and then proceeds to step S104.

In step S104, the control circuit 11*b* notifies the server 13 via the router 12 that the bed apparatus 20 is in a dangerous condition.

Next, in step S105, the control circuit 11*b* determines whether the dangerous condition is able to be resolved by the function of the bed apparatus 20 itself. For example, in a case where the side rails 25 or the casters 26 are able to be locked by using an electrical signal, the control circuit 11*b* determines that the dangerous condition is able to be resolved. If determining that the dangerous condition is able to be resolved, the control circuit 11*b* resolves the dangerous condition and then proceeds to step S106, in which the control circuit 11*b* notifies the server 13 that the problem has been solved.

If, in step S105, determining that the dangerous condition is not able to be resolved by the function of the bed apparatus 20 itself, the control circuit 11*b* proceeds to step S107, in which the control circuit 11*b* determines whether the dangerous condition is able to be resolved by using a robot. The case where the dangerous condition is able to be resolved by using a robot is, for example, a case where the robot is able to be used to apply an external force to a lock mechanism of the side rails 25 or the casters 26 for locking. If determining that the dangerous condition is able to be resolved, the control circuit 11*b* resolves the dangerous condition and then proceeds to step S108, in which the control circuit 11*b* notifies the server 13 that the problem has been solved.

If determining that the dangerous condition is not able to be resolved by using a robot, the control circuit 11*b* proceeds to step S109, in which the control circuit 11*b* determines whether the dangerous condition has been resolved by the terminal user and a dangerous condition resolution check has been passed. An action of the terminal user is described below. If determining that the dangerous condition has been resolved, the control circuit 11*b* proceeds to step S110, in which the control circuit 11*b* notifies the server 13 that the problem has been solved.

If determining that the dangerous condition has not been resolved even by the terminal user, the control circuit 11*b* proceeds to step S111, then, if determining that ten minutes has elapsed, the control circuit 11*b* proceeds to step S112, and, then, if determining that the notification has not been issued ten times, the control circuit 11*b* returns to step S101 to repeat the above-mentioned steps. With this operation, until the dangerous condition is resolved, the control circuit 11*b* issues the notification up to ten times at intervals of ten minutes, and then ends the operation. Furthermore, the interval time for the notification is not limited to ten minutes, and the upper limit of the number of times of the notification is not limited to ten times. These are able to be set by the terminal user.

Next, an operation of the server 13 is described.

In step S201 illustrated in FIG. 5, upon receiving the notification from the control circuit 11*b* of the sensor 11, the server 13 proceeds to step S202, in which the server 13 transmits information about the notification to the mobile terminal 14.

Whether for the server 13 to transmit the notification received from the control circuit 11*b* to the mobile terminal 14 is able to be previously selected by the terminal user and be set via the remote watching application 15 (hereinafter also referred to simply as an "application 15").

In a case where the terminal user performed a setting such that it was necessary to transmit information about the notification to the mobile terminal 14, after receiving the notification from the control circuit 11*b* of the sensor 11, the server 13 proceeds to step S202, in which the server 13 transmits information about the notification to the mobile terminal 14.

In a case where the terminal user performed a setting such that it was not necessary to transmit information about the notification to the mobile terminal 14, even when receiving the notification from the control circuit 11*b* of the sensor 11, the server 13 does not transmit information about the notification to the mobile terminal 14. Alternatively, after the server 13 transmits information about the notification to the mobile terminal 14, the mobile terminal 14 discards the received information automatically.

The information about the notification can be not only information indicating "being in a dangerous condition" but also information indicating "the dangerous condition having been resolved". Thus, whether to transmit a notification of being in a dangerous condition to the mobile terminal 14 and whether to transmit a notification indicating that the dangerous condition has been resolved or there is originally no dangerous condition to the mobile terminal 14 can be previously set by the terminal user.

Next, an operation of the remote watching application 15 and an action of the terminal user are described.

Figure 7A:
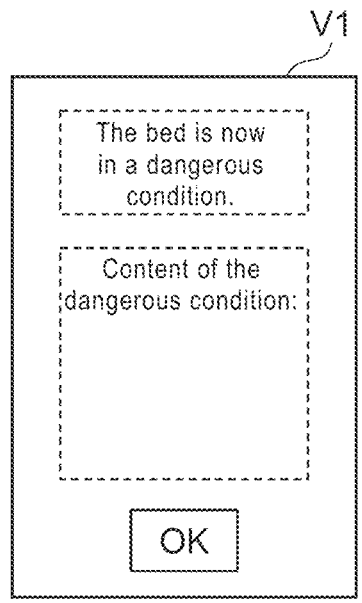
FIGS. 7A, 7B, 7C, and 7D are screen diagrams illustrating screens which a remote watching application according to the embodiment displays on a mobile terminal.

Upon receiving a notification indicating that the bed apparatus 20 is in a dangerous condition from the server 13, the mobile terminal 14 issues a push notification of information about the dangerous condition to the terminal user by the application 15 displaying a screen V1 illustrated in FIG. 7A. At the time of issuing the push notification, the application 15 can use the ring alert and vibration in combination with displaying the screen V1.

In step S301 illustrated in FIG. 6, upon recognizing the screen V1, the terminal user inputs, to the mobile terminal 14, information indicating that the terminal user has become aware of the push notification, for example, by touching an "OK" button in the screen V1. Furthermore, inputting to the mobile terminal 14 by the terminal user is not limited to an operation on the screen, but can be performed, for example, by using voice. The same also applies to subsequent operations.

Figure 7B:
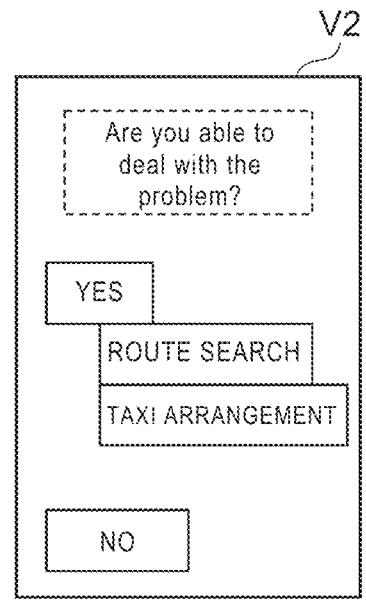

With this inputting, the application 15 displays, for example, a screen V2 illustrated in FIG. 7B to prompt the terminal user to determine whether the terminal user is able to deal with the problem. In step S302 illustrated in FIG. 6, the terminal user determines whether the terminal user is able to deal with the problem, and, if determining that the terminal user is able to deal with the problem, the terminal user touches a "YES" button in the screen V2. At this time, the application 15 can operate in conjunction with a route search application to display a route and a transportation from the current location of the terminal user to a place in which the bed apparatus 20 is present, or can operate in conjunction with a taxi arrangement application to enable arranging for a taxi which is nearest to the current location.

Then, in step S303, the terminal user resolves the dangerous condition by himself/herself. Thus, the terminal user visits the residence of the bed user and operates the bed apparatus 20 to resolve the dangerous condition. For example, if the frame 21 is too heightened, the terminal user moves down the frame 21, and, if the casters 26 are in the unlocked state, the terminal user locks the casters 26. If the side rails 25 are in the storage state, the terminal user brings the side rails 25 into the usage state. If the lock unit 27 is in the unlocked state, the terminal user locks the lock unit 27.

Figure 7C:
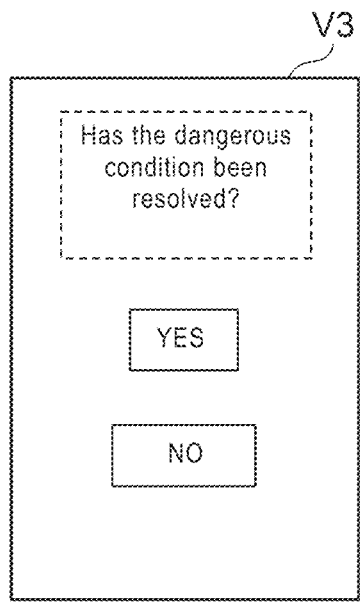

Then, in step S304, the terminal user checks that the dangerous condition has been resolved, and then causes the mobile terminal 14 to display a screen V3 illustrated in FIG. 7C and touches a "YES" button in the screen V3. With this touching, the terminal user inputs information indicating that the dangerous condition has been resolved to the application 15. The server 13 communicates this information to the control circuit 11b of the sensor 11 via the router 12. With this communication, the control circuit 11b selects a determination result "YES" in step S109 illustrated in FIG. 4, and then proceeds to step S110. In this way, a series of operations ends. On the other hand, when the terminal user has touched a "NO" button in the screen V3, the application 15 can support the terminal user by, for example, displaying an instruction manual of the bed apparatus 20.

On the other hand, if, in step S302, determining that the terminal user is not able to deal with the problem, the terminal user touches a "NO" button in the screen V2. This corresponds to, for example, a case where the terminal user is, for example, at work or shopping and is, therefore, unable to immediately go to a place where the bed apparatus 20 is placed.

Figure 7D:
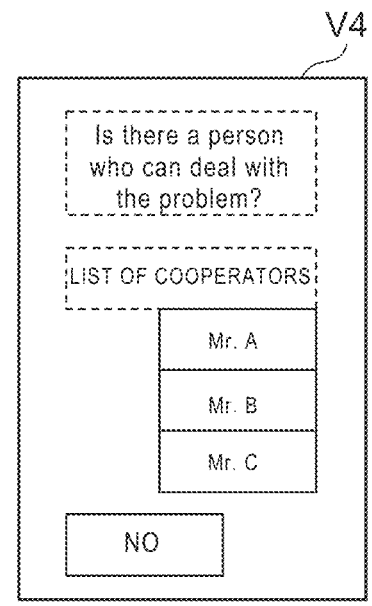

At this time, the application 15 displays a screen V4 illustrated in FIG. 7D to inquire the terminal user whether there is a person who possibly can deal with the problem. For example, the application 15 displays a list of previously registered cooperators. This list can operate in conjunction with a communication application for, for example, telephone, e-mail, or social networking service (SNS) in such a manner that touching the name of a person included in the list enables contacting the person. Moreover, if location information about cooperators is able to be acquired, the application 15 can be configured to additionally display such location information. This enables asking a cooperator who stays closest to the bed apparatus 20 for cooperation. The cooperator can be, whether with or without consideration, for example, a person involved in a private home-visit service company.

In step S305, the terminal user refers to the screen V4 and determines whether there is a person who can deal with the problem. Then, if determining that there is a person who can deal with the problem, the terminal user proceeds to step S306, in which the terminal user contacts and requests the person to resolve the dangerous condition.

If determining that there is no person who can deal with the problem, the terminal user touches a "NO" button in the screen V4 and then proceeds to step S307. Then, the terminal user reads the latest information stored in the server 13 and checks whether the dangerous condition has been automatically resolved. If determining that the dangerous condition has not been automatically resolved, the terminal user proceeds to step S308, in which the terminal user continues a follow-up.

Next, notification of out-of-bed and in-bed of the bed user are described.

Figure 8:
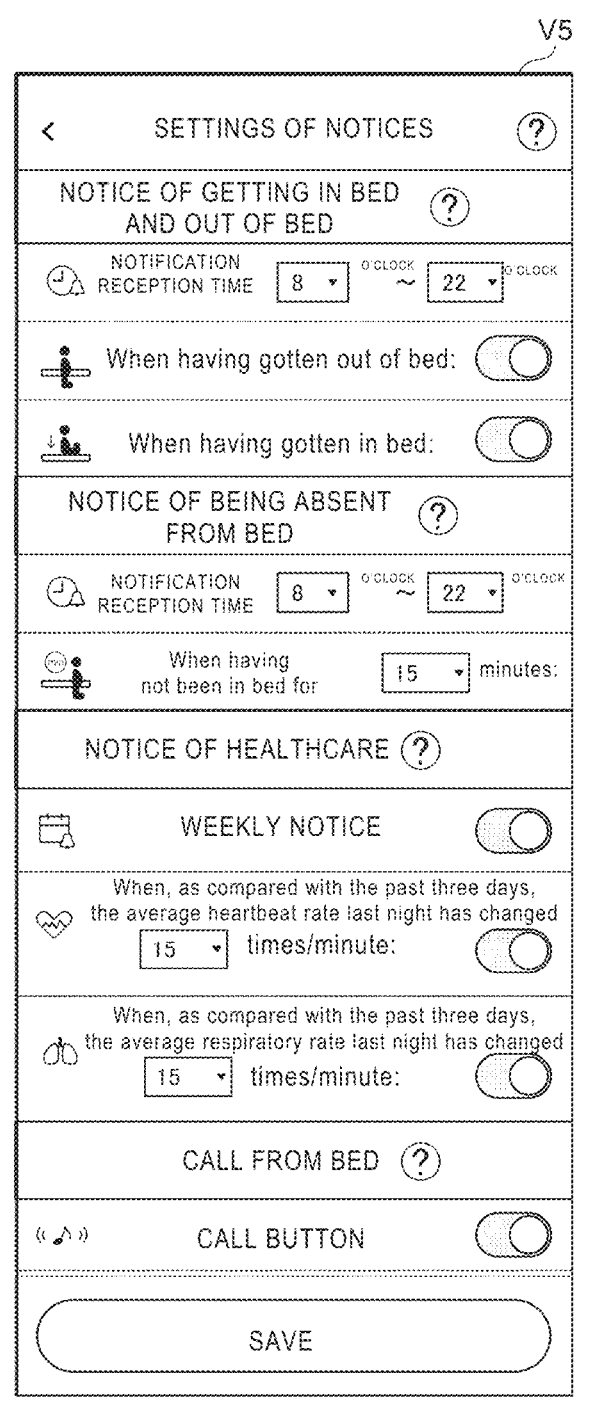

FIG. 8 is a screen diagram illustrating a setting screen of the mobile terminal 14.

Figure 9:
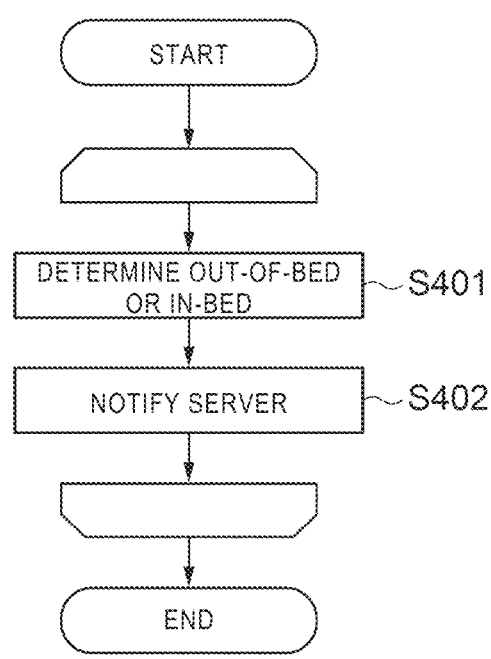
FIG. 9 is a flowchart illustrating an operation of the sensor in notification of out-of-bed and in-bed.

FIG. 9 is a flowchart illustrating an operation of the sensor 11 in notification of out-of-bed and in-bed.

Figure 10:
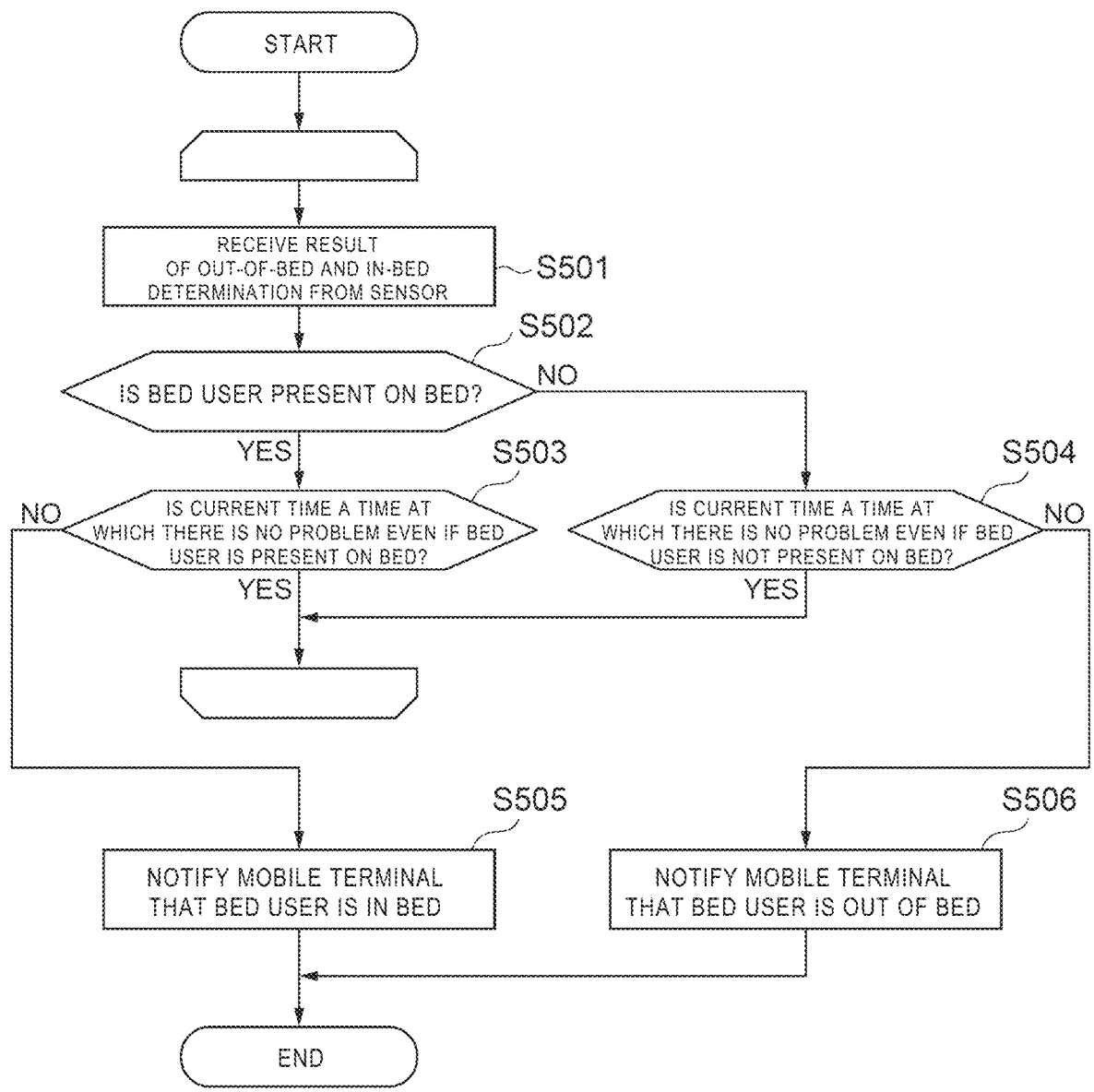
FIG. 10 is a flowchart illustrating an operation of the server in notification of out-of-bed and in-bed.

FIG. 10 is a flowchart illustrating an operation of the server 13 in notification of out-of-bed and in-bed.

Figure 11:
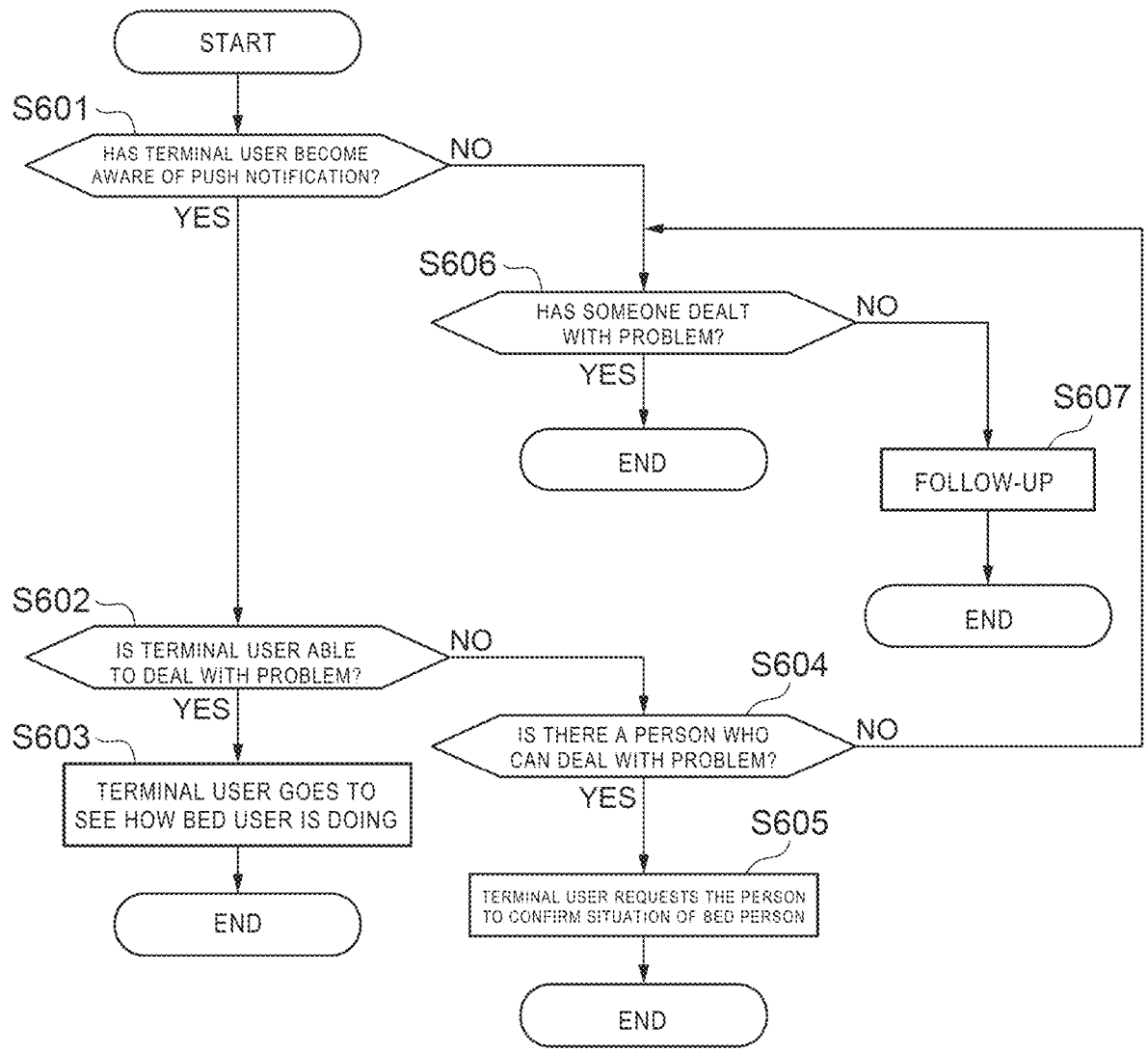
FIG. 11 is a flowchart illustrating an action of the terminal user living together in notification of out-of-bed and in-bed.

FIG. 11 is a flowchart illustrating an action of the terminal user living together in notification of out-of-bed and in-bed.

Figure 12:
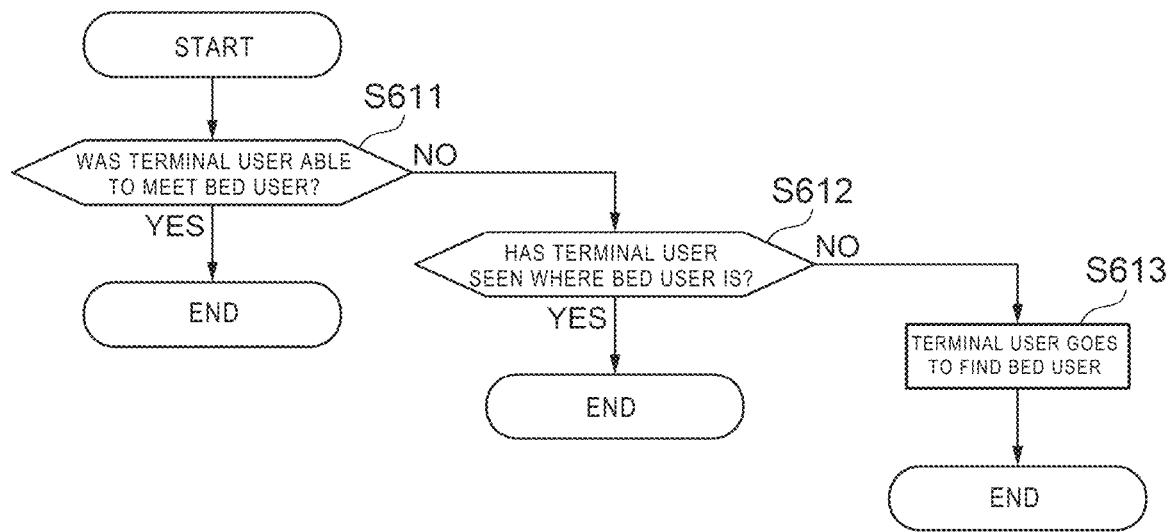
FIG. 12 is a flowchart illustrating an action which the terminal user performs to go to see how a bed user is doing.

FIG. 12 is a flowchart illustrating an action which the terminal user performs to go to see how the bed user is doing.

Figure 13:
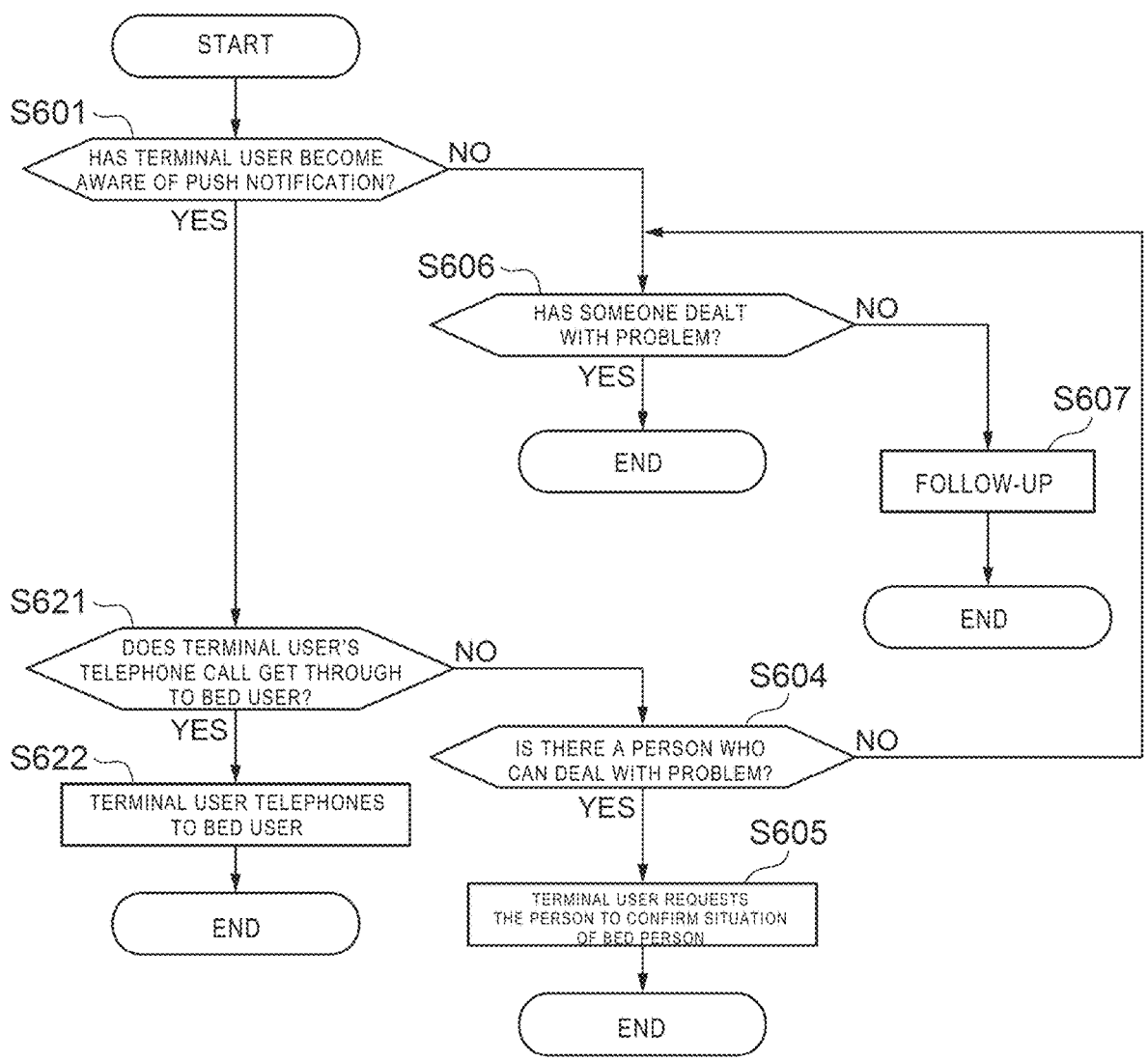
FIG. 13 is a flowchart illustrating an action of the terminal user living apart in notification of out-of-bed and in-bed.

FIG. 13 is a flowchart illustrating an action of the terminal user living apart in notification of out-of-bed and in-bed.

Figure 14:
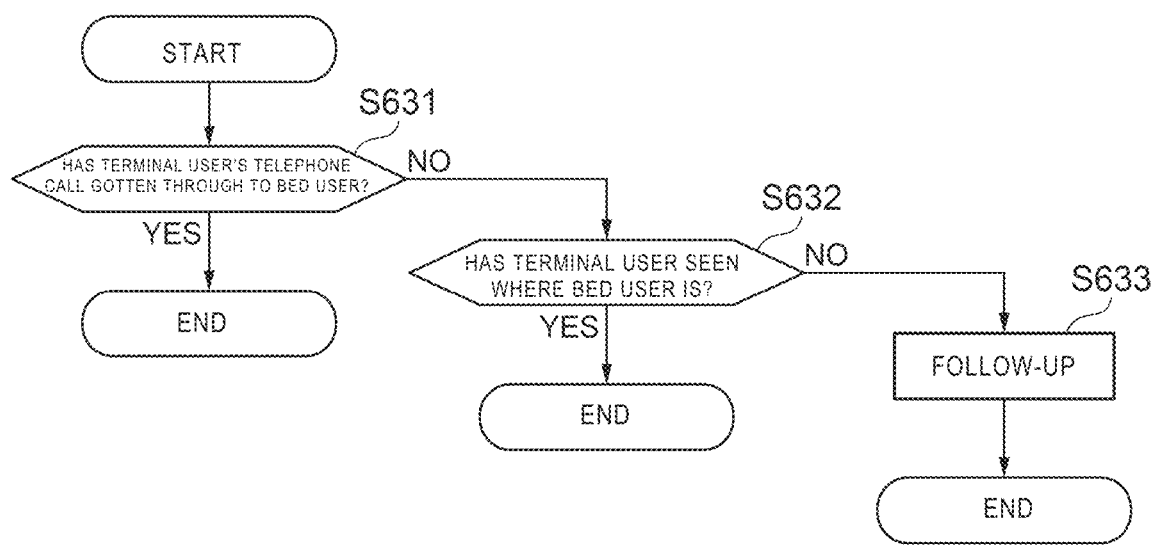
FIG. 14 is a flowchart illustrating an action which the terminal user performs to telephone to the bed user.

FIG. 14 is a flowchart illustrating an action which the terminal user performs to telephone to the bed user.

FIGS. 15A, 15B, 15C, and 15D are screen diagrams illustrating screens which the remote watching application 15 according to the present embodiment displays on the mobile terminal 14.

As illustrated in FIG. 8, the terminal user previously operates a screen V5 displayed on the mobile terminal 14 and performs settings concerning notification. For example, the terminal user performs settings concerning, for example, whether to receive a notification when the bed user has gotten out of the bed apparatus 20 and when the bed user has gotten into the bed apparatus 20, a reception time period for receiving the notification, a reception time period for receiving a notification of out-of-bed, whether a weekly history about the physical condition of the bed user is needed, a condition on which to receive a notification when the physical condition of the bed user has changed, and whether to receive a call from the bed user.

The settings can be made different depending on whether the terminal user is living with the bed user or living apart from the bed user. Moreover, the settings can be made different depending on whether, even if the terminal user is living apart from the bed user, the terminal user is residing at a place from which the terminal user is able to readily visit the residence of the bed user as needed ("living nearby") or the terminal user is residing at a place from which the terminal user is unable to readily visit the residence of the bed user ("living distantly"). In this case, the application 15 can be configured to estimate the location of the terminal user based on the location information about the mobile terminal 14 and automatically change whether the terminal user is "living nearby" or "living distantly". Thus, in a case where the terminal user has moved from a place from which the terminal user is able to readily visit the residence of the bed user to a place from which the terminal user is unable to readily visit the residence of the bed user, the application 15 can automatically change the settings from settings for "living nearby" to settings for "living distantly".

Moreover, the settings can be made different depending on a relationship between the terminal user and the bed user. The settings can be made different depending on, for example, a case where the terminal user is a family member of the bed user, a case where the terminal user is a friend of the bed user, a case where the terminal user is a care manager, and a case where the terminal user is a caretaker involved in a company which provides nursing services (a certified care worker, a home care worker, or an in-home caregiver).

The terminal user can previously perform a setting such that the terminal user is able to receive only necessary notifications within a desired time period. States required for notification include not only a state in which the bed user is at risk or is abnormal but also a state in which the bed user is normal. A notification of the state in which the bed user is normal can be transmitted when the terminal user has inquired the server 13 via the mobile terminal 14 or can be transmitted at the previously set clock time.

In a case where the terminal user is a caretaker, the terminal user is able to upload caregiving date and time and caregiving content to the server 13, as described below. In this case, the notification can be transmitted after a predetermined length of time elapses from the date and time of the last caregiving based on the uploaded information about caregiving. For example, the terminal user can perform setting such that no notification is transmitted until 24 hours elapses from ending of caregiving. Moreover, the terminal user can perform a setting of not transmitting a notification, based on location information about the caretaker. For example, when the caretake is just caring for the bed user, no notification is transmitted. Moreover, the terminal user is able to select the terminal user's own attribute, and can previously determine an initial value for the setting to be communicated as a notification for the selected attribute. Furthermore, even after the setting is once performed with an initial value, the content of the setting can be freely changed.

On the other hand, there is a case where a state in which the bed user is at risk had better be communicated as a notification regardless of the setting. Therefore, a notification for communicating a state in which the bed user is at risk can be forcibly transmitted even in a time period other than a previously set desired time period. In that case, even if the mobile terminal 14 is set not to emit a sound at the time of issuing a push notification, a sound can be forcibly emitted. Moreover, in a case where the terminal user is present at the side of the bed user, a notification can be made temporarily null. For example, a configuration in which a button indicating "visit in progress" is displayed on the screen of the mobile terminal 14 and pressing the button makes a notification temporarily null can be employed.

First, an operation of the control circuit 11b of the sensor 11 is described.

First, in step S401 illustrated in FIG. 9, the control circuit 11b performs out-of-bed and in-bed determination about the bed user. The method for out-of-bed and in-bed determination is the same as that descriat described in step S102 illustrated in FIG. 4.

Next, in step S402, the control circuit 11b notifies the server 13 via the router 12 of a result of the out-of-bed and in-bed determination.

After that, the control circuit 11b repeats steps S401 and S402.

Whether for the server 13 to transmit a notification received from the control circuit 11b to the mobile terminal 14 is able to be previously selected and set by the terminal user.

In a case where the terminal user previously performed such a setting as to require information about the notification to be transmitted to the mobile terminal 14, the server 13 receives the notification from the control circuit 11b of the sensor 11 and then proceeds to step S202, in which the server 13 transmits information about the notification to the mobile terminal 14.

In a case where the terminal user previously performed such a setting as not to require information about the notification to be transmitted to the mobile terminal 14, even when receiving the notification from the control circuit 11b of the sensor 11, the server 13 does not transmit information about the notification to the mobile terminal 14. Alternatively, the server 13 transmits information about the notification to the mobile terminal 14 and, then, the mobile terminal 14 automatically discards the received information.

Next, an operation of the server 13 is described.

In step S501 illustrated in FIG. 10, the server 13 receives a result of the out-of-bed and in-bed determination from the sensor 11, and then proceeds to step 3502, in which, if the bed user is present on the bed apparatus 20, the server 13 proceeds to step S503 and, if the bed user is not present on the bed apparatus 20, the server 13 proceeds to step S504.

If the bed user is present on the bed apparatus 20, then in step S503, the server 13 determines whether the current time is a time at which there is no problem even if the bed user is present on the bed apparatus 20. The time at which there is no problem even if the bed user is present on the bed apparatus 20 is, for example, a time period including nighttime. Depending on the situation of the bed user, to prevent a day-night reversal phenomenon, it is recommended that the bed user be out of bed for a predetermined time period in the daytime, for example, a time period from 10 o'clock to 16 o'clock. In this case, the time at which there is no problem even if the bed user is present on the bed apparatus 20 is a time period from 16 o'clock to next day 10 o'clock. If the current time is a time at which there is no problem even if the bed user is present on the bed apparatus 20, the server 13 returns to step S501. If the current time is not a time at which there is no problem even if the bed user is present on the bed apparatus 20, for example, if the current time is included in a time period from 10 o'clock to 16 o'clock, in which out-of-bed is recommended, the server 13 proceeds to step S505, in which the server 13 notifies the mobile terminal 14 that the bed user is in bed. Furthermore, the server 13 can acquire time information (clock time information) for use in determining whether the current time is a time at which there is no problem even if the bed user is present on the bed apparatus 20 from the server 13 itself, can acquire the time information from the mobile terminal 14, can acquire the time information by accessing, for example, a clock time supply service via an Internet line, or can acquire the time information by using any other method.

Whether for the server 13 to notify the mobile terminal 14 that the bed user is in bed is able to be previously selected and set by the terminal user.

In a case where the terminal user previously performed such a setting as to require the mobile terminal 14 to be notified that the bed user was in bed, if receiving a result of the out-of-bed and in-bed determination from the sensor 11, the server 13 proceeds to step S505, in which the server 13 notifies the mobile terminal 14 of the received result.

In a case where the terminal user previously performed such a setting as not to require the mobile terminal 14 to be notified that the bed user was in bed, even when receiving a result of the out-of-bed and in-bed determination from the sensor 11, the server 13 does not notify the mobile terminal 14 of the result of the out-of-bed and in-bed determination. Alternatively, the server 13 notifies the mobile terminal 14 of a result of the out-of-bed and in-bed determination and, then, the mobile terminal 14 automatically discards the result of the out-of-bed and in-bed determination.

If the bed user is not present on the bed apparatus 20, then in step S504, the server 13 determines whether the current time is a time at which there is no problem even if the bed user is not present on the bed apparatus 20. The time at which there is no problem even if the bed user is not present on the bed apparatus 20 is, for example, a time period including daytime. Since it is ordinarily recommended that the bed user get out of bed in the morning and go to bed at night, for example, a time period from 5 o'clock in the morning to 23 o'clock at night is a time period for which there is no problem even if the bed user is not present on the bed apparatus 20. If the current time is a time at which there is no problem even if the bed user is not present on the bed apparatus 20, the server 13 returns to step S501. If the current time is not a time at which there is no problem even if the bed user is not present on the bed apparatus 20, for example, if the current time is included in a time period from 23 o'clock to next day 5 o'clock, in which in-bed is recommended, the server 13 proceeds to step S506, in which the server 13 notifies the mobile terminal 14 that the bed user is out of bed. Furthermore, the server 13 can acquire time information (clock time information) for use in determining whether the current time is a time at which there is no problem even if the bed user is not present on the bed apparatus 20 from the server 13 itself, can acquire the time information from the mobile terminal 14, can acquire the time information by accessing, for example, a clock time supply service via an Internet line, or can acquire the time information by using any other method.

Whether for the server 13 to notify the mobile terminal 14 that the bed user is out of bed is able to be previously selected and set by the terminal user.

In a case where the terminal user previously performed such a setting as to require the mobile terminal 14 to be notified that the bed user was out of bed, if receiving a result of the out-of-bed and in-bed determination from the sensor 11, the server 13 proceeds to step S506, in which the server 13 notifies the mobile terminal 14 of the received result.

In a case where the terminal user previously performed such a setting as not to require the mobile terminal 14 to be notified that the bed user was out of bed, even when receiving a result of the out-of-bed and in-bed determination from the sensor 11, the server 13 does not notify the mobile terminal 14 of the result of the out-of-bed and in-bed determination. Alternatively, the server 13 notifies the mobile terminal 14 of a result of the out-of-bed and in-bed determination and, then, the mobile terminal 14 automatically discards the result of the out-of-bed and in-bed determination.

Next, an operation of the remote watching application 15 and an action of the terminal user are described.

First, a case where the terminal user is living with the bed user is described.

Figure 15A:
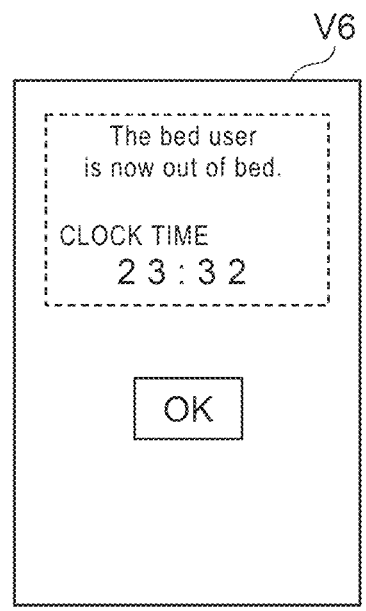
FIGS. 15A, 15B, 15C, and 15D are screen diagrams illustrating screens which a remote watching application according to the embodiment displays on the mobile terminal.

When the mobile terminal 14 receives a notification indicating that the bed user is in bed or out of bed from the server 13, the application 15 displays a screen V6 illustrated in FIG. 15A to issue a push notification indicating information about the received notification to the terminal user. While, in the following description, a case where the bed user is out of bed in a time period for which it is recommended that the bed user be in bed is described as an example, the same also applies to a case where the bed user is in bed in a time period for which it is recommended that the bed user be out of bed.

In step S601 illustrated in FIG. 11, upon recognizing the screen V6, the terminal user inputs, to the mobile terminal 14, information indicating that the terminal user has become aware of the push notification, by touching an "OK" button in the screen V6.

Figure 15B:
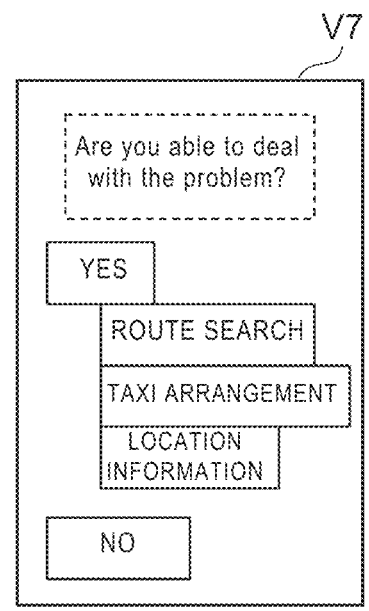

With this inputting, the application 15 displays, for example, a screen V7 illustrated in FIG. 15B to prompt the terminal user to determine whether the terminal user is able to deal with the problem. In step S602 illustrated in FIG. 11, the terminal user determines whether the terminal user is able to deal with the problem, and, if determining that the terminal user is able to deal with the problem, the terminal user touches a "YES" button in the screen V7.

Next, in step S603 illustrated in FIG. 11, the terminal user goes to see how the bed user is doing. If the terminal user is living with the bed user, this is easy. However, even if the terminal user is living with the bed user, when the terminal user is not home due to circumstances such as having gone to work, the terminal user is required to immediately come home. In this case, the application 15 can operate in conjunction with a taxi arrangement application to enable arranging for a taxi which is nearest to the current location. Moreover, if location information about the bed user is able to be acquired, the application 15 can be configured to additionally display such location information. This also enables determining that, as long as the bed user is in home although being out of bed, there is little danger and the terminal user does not need to take the trouble of going to see how the bed user is doing.

Figure 15C:
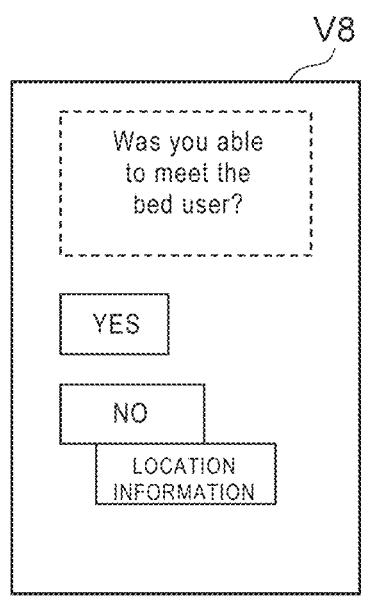

The application 15 displays a screen V8 illustrated in FIG. 15C to check whether the terminal user was able to meet the bed user. Then, in step S611 illustrated in FIG. 12, if the terminal user was able to meet the bed user, the terminal user checks the situation of the bed user and, then, ends the action.

On the other hand, if the terminal user was not able to meet the bed user, then in step S612 illustrated in FIG. 12, the terminal user determines whether the terminal user has seen the location of the bed user. Even in this case, if the application 15 is able to use location information about the bed user, the application 15 can display the location information to support the terminal user. If the terminal user has seen where the bed user is, the terminal user goes to see how the bed user is doing, as needed, and then ends the action. If the terminal user has not seen where the bed user is, then in step S613, the terminal user goes to find the bed user.

On the other hand, if, in step S602 illustrated in FIG. 11, determining that the terminal user is not able to deal with the problem, the terminal user touches a "NO" button in the screen V7 illustrated in FIG. 15B. This corresponds to a case where the terminal user is not home and is not able to immediately come home.

Figure 15D:
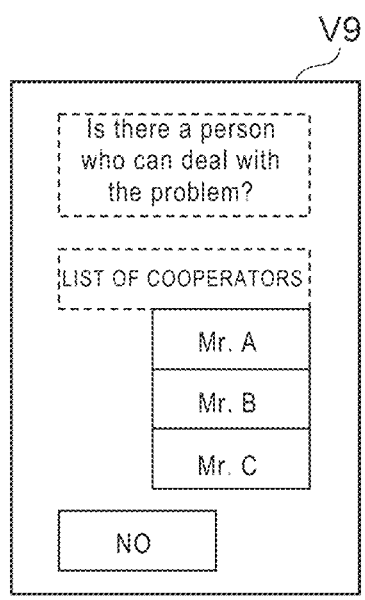

At this time, the application 15 displays a screen V9 illustrated in FIG. 15D to inquire the terminal user whether there is a person who possibly can deal with the problem other than the terminal user. For example, the application 15 displays a list of previously registered cooperators. This list can operate in conjunction with a communication application in such a manner that touching the name of a person included in the list enables contacting the person. Moreover, if location information about cooperators is able to be acquired, the application 15 can be configured to additionally display such location information. This enables asking a cooperator who stays closest to the residence of the bed user for cooperation. The cooperator can be, whether with or without consideration, for example, a person involved in a private home-visit service company.

In step S604, the terminal user refers to the screen V9 and determines whether there is a person who can deal with the problem. Then, if determining that there is a person who can deal with the problem, the terminal user proceeds to step S605, in which the terminal user contacts and requests the person to confirm the situation of the bed user.

If determining that there is no person who can deal with the problem, then in step S606, the terminal user checks whether someone has dealt with the problem. If determining that no one has dealt with the problem, the terminal user proceeds to step S607, in which the terminal user continues a follow-up.

Next, a case where the terminal user is living apart from the bed user is described. In this case, it is supposed that the terminal user is not able to go to meet the bed user and contacts the bed user by telephone.

As illustrated in FIG. 13, the action of the terminal user living apart from the bed user differs from the action of the terminal user living with the bed user illustrated in FIG. 11 in that the terminal user performs steps S621 and S622 instead of steps S602 and S603.

In step S601 illustrated in FIG. 13, if the terminal user has become aware of a notification indicating that the bed user is out of bed and has input information about the notification to the mobile terminal 14, the application 15 can activate a verbal communication function and display the phone number of the bed user. This enables the terminal user to telephone to the bed user. Then, in step S621, the terminal user determines whether the terminal user's telephone call gets through to the bed user, and, if determining that the terminal user's telephone call gets through to the bed user, then in step S622, the terminal user telephones to the bed user. In step S631 illustrated in FIG. 14, if the terminal user's telephone call has gotten through to the bed user, the terminal user checks the situation of the bed user and then ends the action.

On the other hand, if the terminal user's telephone call has not gotten through to the bed user, then in step S632, the terminal user determines whether the terminal user has seen the location of the bed user. Even in this case, if there is location information about the bed user, the terminal user is able to use the location information. Moreover, a human-presence sensor or a camera can be placed near a table at which the bed user eats meals, in a toilet, or in a bathroom. This enables knowing the whereabouts of the bed user having been out of bed. If having seen where the bed user is, the terminal user ends the action. Alternatively, the terminal user can be allowed to remotely manipulate facilities in the residence of the bed user. For example, the terminal user can increase lighting in a place where the bed user is present. Moreover, the terminal user can lock the front door of the residence of the bed user to prevent the bed user to wander.

On the other hand, if the terminal user has not seen the whereabouts of the bed user, then in step S633, the terminal user performs a follow-up. Furthermore, the application 15 can be configured to make a search of the area around the residence of the bed user with use of a robot or a drone, or can be configured to be able to check, by remote control, video images captured by cameras placed inside and outside the residence of the bed user.

If the terminal user's telephone call does not get through to the bed user, the terminal user proceeds from step S621 to step S604, in which the terminal user asks a cooperator for support, as with the case of the terminal user living with the bed user. A subsequent action of the terminal user is similar to that of the terminal user living with the bed user.

Next, notifications of changes of the heartbeat rate and respiratory rate of the bed user are described.

Figure 16:
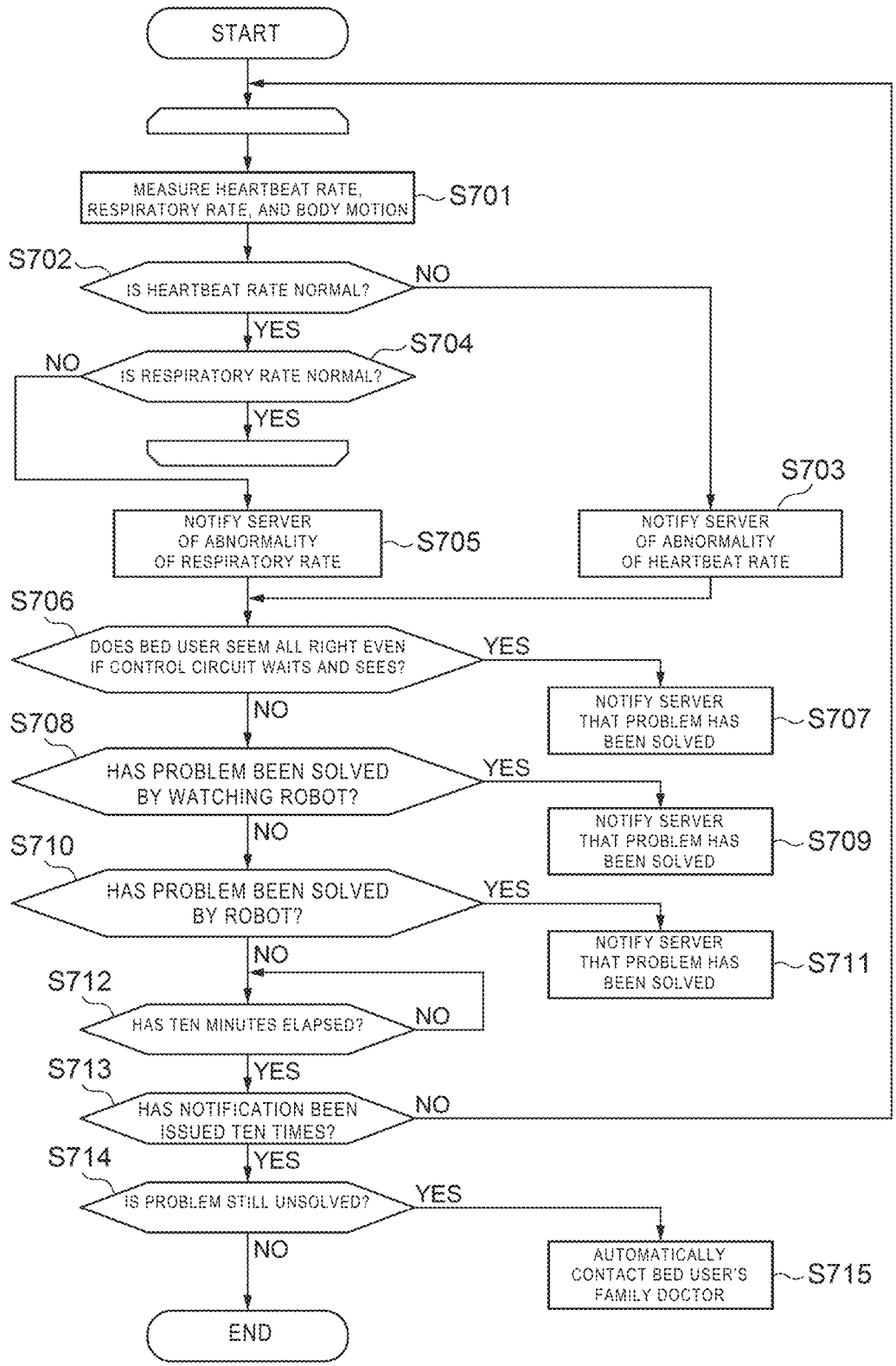
FIG. 16 is a flowchart illustrating an operation of the sensor in notification of changes in heartbeat rate and respiratory rate.

FIG. 16 is a flowchart illustrating an operation of the sensor 11 in notification of changes in heartbeat rate and respiratory rate.

Figure 17:
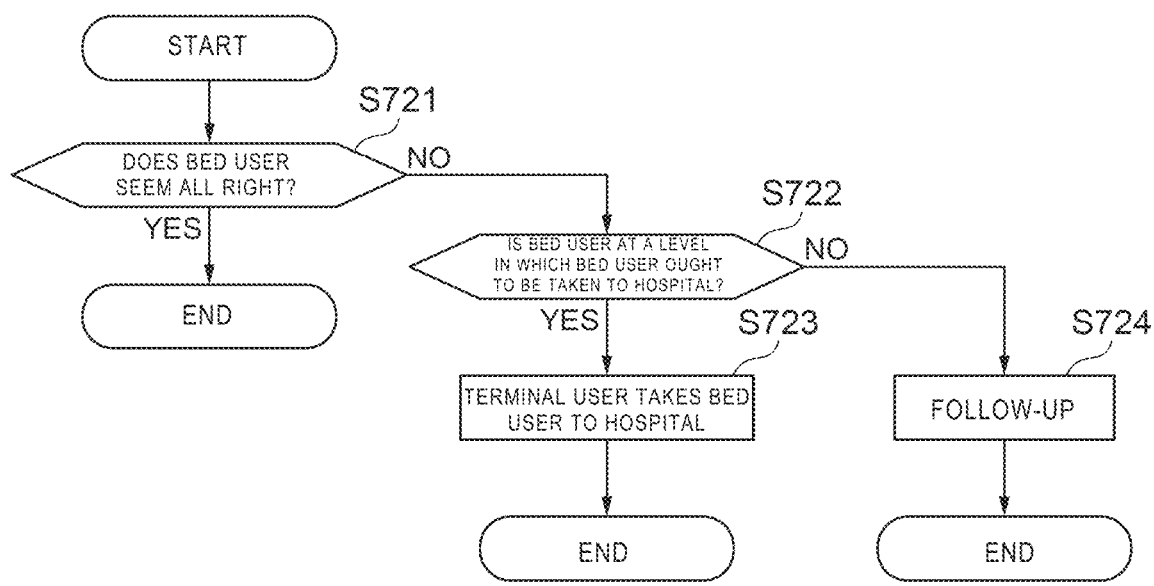
FIG. 17 is a flowchart illustrating an action which the terminal user performs to go to see how the bed user is doing.

FIG. 17 is a flowchart illustrating an action which the terminal user performs to go to see how the bed user is doing.

Figure 18:
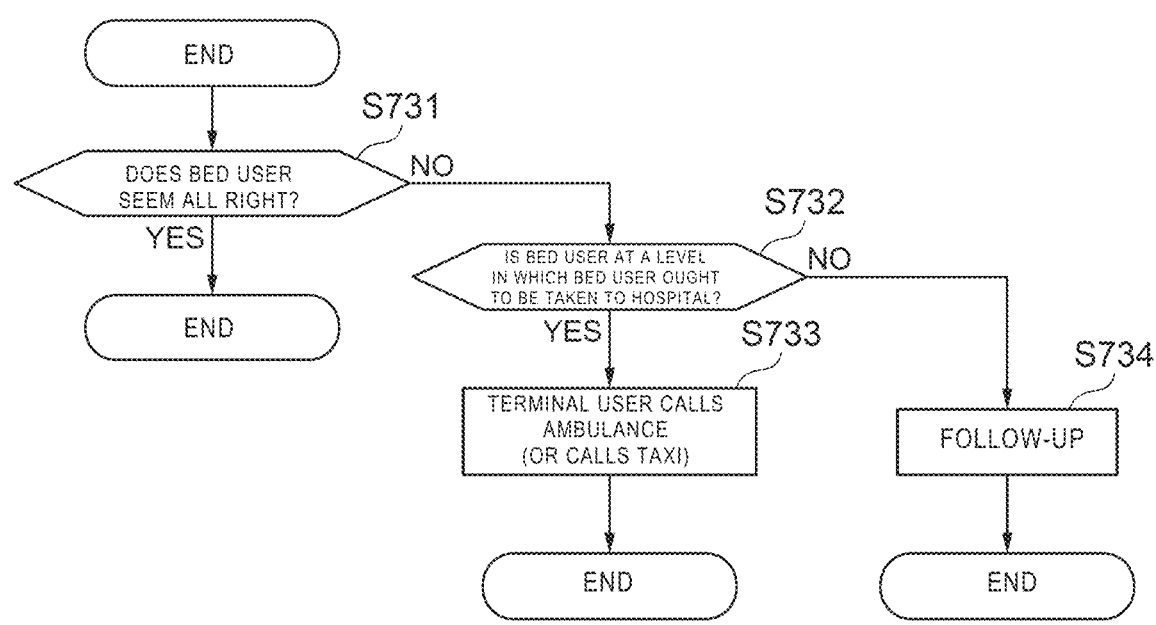
FIG. 18 is a flowchart illustrating an action which the terminal user performs to telephone to the bed user.
Figure 19A:
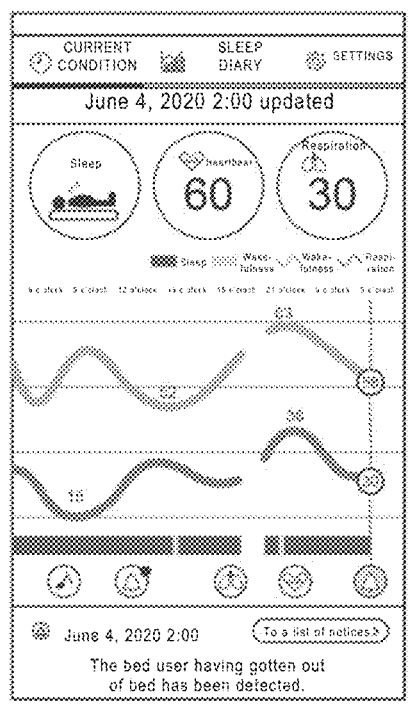
FIGS. 19A, 19B, 19C, and 19D are screen diagrams illustrating healthcare reports which the remote watching application according to the embodiment provides.
Figure 19B:
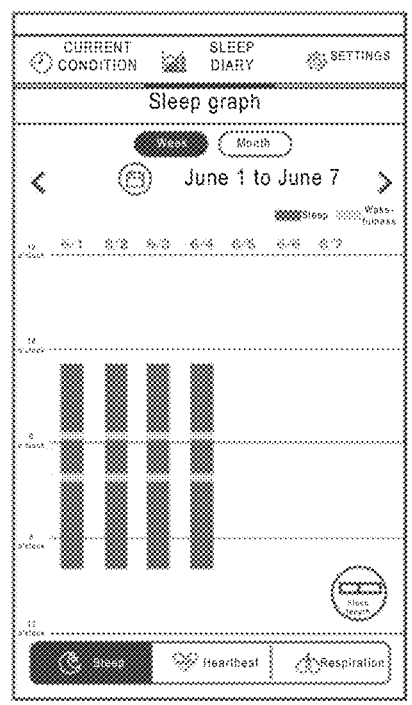
Figure 19C:
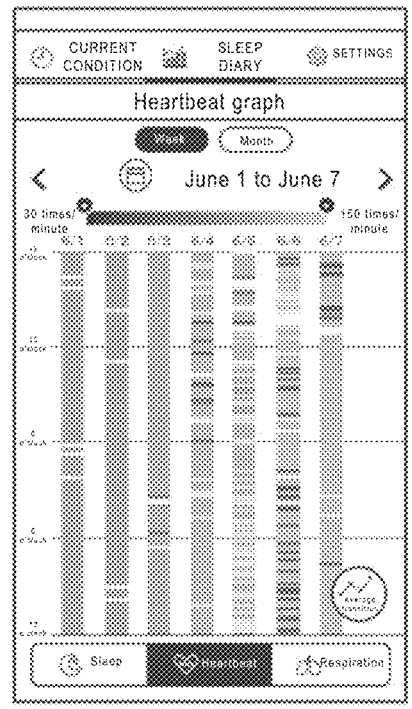
Figure 19D:
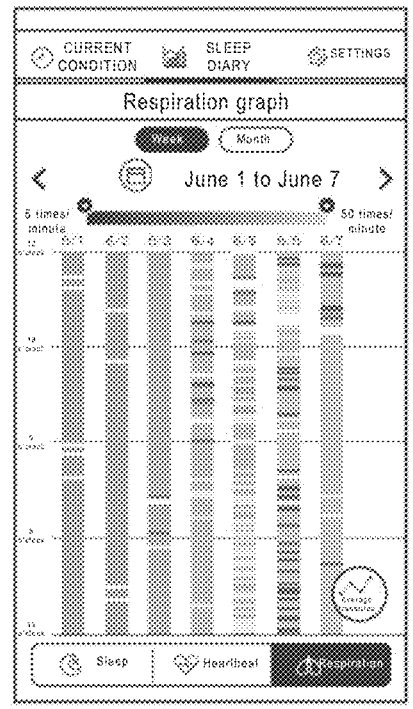

FIG. 18 is a flowchart illustrating an action which the terminal user performs to telephone to the bed user.

First, an operation of the control circuit 11b of the sensor 11 is described.

In step S701 illustrated in FIG. 16, the sensor 11 measures the heartbeat rate, respiratory rate, and body motion of the bed user.

Next, in step S702, the control circuit 11b determines whether the heartbeat rate is normal. If determining that the heartbeat rate is not normal, the control circuit 11b proceeds to step S703, in which the control circuit 11b notifies the server 13 of an abnormality of the heartbeat rate.

If determining that the heartbeat rate is normal, the control circuit 11b proceeds to step S704, in which the control circuit 11b determines whether the respiratory rate is normal. If determining that the respiratory rate is not normal, the control circuit 11b proceeds to step S705, in which the control circuit 11b notifies the server 13 of an abnormality of the respiratory rate.

If determining that both the heartbeat rate and the respiratory rate are normal, the control circuit 11b returns to step S701 and then repeats operations in steps S701 to S704 at a predetermined interval. On the other hand, after performing each of steps S703 and S705, the control circuit 11b proceeds to step S706.

In step S706, the control circuit 11b measures the body temperature of the bed user with a non-contact clinical thermometer. Moreover, the control circuit 11b observes the face of the bed user with a camera. The camera is connected to the control circuit 11b of the sensor 11 and detects changes in the color of the face and the expression on the face of the bed user by previously learning the usual face of the bed user. Then, the control circuit 11b determines whether, even if the control circuit 11b waits and sees, the bed user seems all right, based on a result of measurement of the body temperature and a result of observation of the face of the bed user. If determining that, even if the control circuit 11b waits and sees, the bed user seems all right, the control circuit 11b proceeds to step 3707, in which the control circuit 11b notifies the server 13 that the problem has been solved.

If determining that, if the control circuit 11b waits and sees, the bed user does not seem all right, the control circuit 11b proceeds to step S708, in which the control circuit 11b tries a solution using a watching robot. The watching robot is not equipped with any movable portion and deals with the bed user by voice. For example, the watching robot provides a greeting to the bed user. If determining that the problem has been solved by the watching robot, the control circuit 11b proceeds to step S709, in which the control circuit 11b notifies the server 13 that the problem has been solved.

If determining that the problem has not been solved by the watching robot, the control circuit 11b proceeds to step S710, in which the control circuit 11b tries a solution using a robot. The robot is equipped with a movable portion and is able to, for example, get the bed user a cup of water. If determining that the problem has been solved by the robot, the control circuit 11b proceeds to step S711, in which the control circuit 11b notifies the server 13 that the problem has been solved.

If determining that the problem has not been solved even by the robot, the control circuit 11b proceeds to step S712, then, if determining that ten minutes has elapsed, the control circuit 11b proceeds to step S713, and, then, if determining that the notification has not been issued ten times, the control circuit 11b returns to step S701 to repeat the above-mentioned steps. With this operation, until the problem is solved, the control circuit 11b issues the notification up to ten times at intervals of ten minutes, and then ends the operation. Furthermore, the interval time for the notification is not limited to ten minutes, and the upper limit of the number of times of the notification is not limited to ten times. These are able to be set by the terminal user.

In step S714, if determining that, even when the notification has been issued ten times, the problem has not yet been solved, the control circuit 11b proceeds to step S715, in which the control circuit 11b automatically contacts the bed user's family doctor.

An operation of the server 13 is similar to the operation described with reference to FIG. 5. Thus, upon receiving the notification from the sensor 11, the server 13 notifies the mobile terminal 14. Whether for the server 13 to notify the mobile terminal 14 is able to be previously selected and set by the terminal user. In a case where the terminal user performed a setting such that it was necessary for the server 13 to notify the mobile terminal 14, upon receiving the notification from the sensor 11, the server 13 notifies the mobile terminal 14. In a case where the terminal user performed a setting such that it was not necessary for the server 13 to notify the mobile terminal 14, even when receiving the notification from the sensor 11, the server 13 does not notify the mobile terminal 14. Alternatively, after the server 13 notifies the mobile terminal 14, the mobile terminal 14 automatically discards the received notification.

An operation of the application 15 and an action of the terminal user are similar to the actions illustrated in FIG. 11 and FIG. 13. Thus, if the mobile terminal 14 is notified by the server 13 of the abnormality of the heartbeat rate or the abnormality of the respiratory rate and is not notified that the problem has been solved, the application 15 performs a push notification. When the terminal user has become aware of the push notification, the terminal user goes to see how the bed user is doing or tries to contact the bed user by telephone, and, if this is difficult, the terminal user asks a cooperator for checking and, if this is still difficult, the terminal user performs a follow-up. However, even when the terminal user performs a follow-up, in step S715 illustrated in FIG. 16, after performing predetermined steps, the remote watching system 1 automatically contacts the bed user's family doctor. The cooperator can be, whether with or without consideration, for example, a person involved in a private home-visit service company.

If the terminal user has gone to see how the bed user is doing, in step S721 illustrated in FIG. 17, the terminal user determines whether the bed user seems all right. If determining that the bed user seems all right, the terminal user then ends the action. If determining that the bed user does not seem all right, the terminal user proceeds to step S722, in which the terminal user determines whether the bed user is at a level in which the bed user ought to be taken to a hospital. If determining that the bed user is at a level in which the bed user ought to be taken to a hospital, the terminal user proceeds to step S723, in which the terminal user takes the bed user to the hospital. If determining that the bed user is not at a level in which the bed user ought to be taken to a hospital, the terminal user proceeds to step S724, in which the terminal user performs a follow-up.

In a case where the terminal user has telephoned to the bed user, then in step S731 illustrated in FIG. 18, the terminal user determines whether the bed user seems all right. If determining that the bed user seems all right, the terminal user then ends the action. If determining that the bed user does not seem all right, the terminal user proceeds to step S732, in which the terminal user determines whether the bed user is at a level in which the bed user ought to be taken to a hospital. If determining that the bed user is at a level in which the bed user ought to be taken to a hospital, the terminal user proceeds to step S733, in which the terminal user calls an ambulance or a taxi. If determining that the bed user is not at a level in which the bed user ought to be taken to a hospital, the terminal user proceeds to step S734, in which the terminal user performs a follow-up.

Furthermore, in a case where the terminal user is a caretaker and is caring for the bed user regardless of the presence or absence of a notification, the terminal user is able to upload, to the server 13, the day of visit, the clock time of starting care, the clock time of ending care, a length of time of care, and the content of care.

Next, healthcare reports are described.

FIGS. 19A, 19B, 19C, and 19D are screen diagrams illustrating healthcare reports which the remote watching application 15 according to the present embodiment provides.

As illustrated in FIGS. 19A to 19D, even if the bed user does not particularly reveal any abnormality, the application 15 periodically creates a report indicating the physical condition of the bed user, and presents the created report to the terminal user. The report contains, for example, the sleeping condition, changes in heartbeat rate, and changes in respiratory rate of the bed user. The time interval at which to create reports is able to be set by the terminal user, and, for example, is able to be set to every week or every month.

Next, advantageous effects of the present embodiment are described.

In the remote watching system 1 according to the present embodiment, the server 13 is able to acquire bed information from the bed apparatus 20, acquire biological information about the bed user from the sensor 11, and determine the condition of the bed user based on the acquired bed information and biological information. This enables making an accurate determination without human intervention. Moreover, notifying the mobile terminal 14 of a result of determination enables the terminal user to receive information about the result of determination even when the terminal user stays away from the bed user. Additionally, the sensor 11 or the server 13 making a determination up to some degree enables decreasing the frequency of the mobile terminal 14 performing a push notification, and thus enables reducing a burden on the terminal user while ensuring the safety of the bed user. As a result, the remote watching system 1 is able to appropriately care for a person requiring support with a reduced burden.

Moreover, installing the dedicated application 15 on the mobile terminal 14 enables improving operability and visibility for the terminal user. Moreover, the application 15 operating in conjunction with other applications, such as a communication application, a location information application, a route search application, and a taxi arrangement application enables supporting an action of the terminal user.

Additionally, even when an abnormality has occurred in the bed user, the application 15 sequentially displaying screens along a predetermined flowchart and prompting the terminal user to make a determination enables guiding the terminal user, who is not necessarily a specialist on nursing care, to an appropriate action. In this case, the application 15 can display a plurality of options on the mobile terminal 14 and additionally display a word such as "recommended" with respect to a recommended option.

Furthermore, while, in the present embodiment, an example in which the bed user and the terminal user are set on a one-to-one basis has been described, the present embodiment is not limited to this. The bed user and the terminal user can be set on a plurality-to-one basis. For example, this is a case where one son or daughter watches over the condition of each of his or her both parents. Moreover, the bed user and the terminal user can be set on a one-to-plurality basis. For example, this is a case where a plurality of sons or daughters watches over their one person. Additionally, the bed user and the terminal user can be set on a plurality-to-plurality basis. For example, this is a case where a plurality of sons or daughters watches over the conditions of their both parents or a case where a community forms a support network with respect to a plurality of aged persons in the community.

Moreover, while, in the present embodiment, an example in which the bed apparatus 20 and the sensor 11 are placed in the residence of the bed user has been described, the present embodiment is not limited to this, and the bed apparatus 20 and the sensor 11 can be placed in a hospital or nursing-care facility. In this case, the terminal user is, for example, a nurse working for the hospital or a careworker working for the nursing-care facility.

The above-described embodiment is an example obtained by embodying the present disclosure, and the present disclosure is not limited to this embodiment. For example, embodiments obtained by adding, deleting, or altering some constituent elements or steps in the above-described embodiment are also included in the present disclosure.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A remote watching system comprising:
    a sensor attached to a bed apparatus and configured to acquire biological information about a bed user who uses the bed apparatus;
    a server configured to receive the biological information from the sensor and output a notification that is based on the biological information; and
    a mobile terminal configured to receive the notification and display the received notification, wherein
    the server outputs only a previously set notification or the mobile terminal displays only a previously set notification, and
    the server automatically sets a notification to be output and a time period for which to output the notification, depending on an attribute of a user of the mobile terminal.

2. The remote watching system according to claim 1, wherein the server outputs the notification for a previously set time period or the mobile terminal displays the notification for the previously set time period.

3. The remote watching system according to claim 1, wherein a light emitter of a user interface device of the bed apparatus turns on or blinks according to information input to the mobile terminal.

4. The remote watching system according to claim 1, wherein the sensor further acquires bed information about the bed apparatus, and
    wherein the notification is based on the biological information and the bed information.

5. The remote watching system according to claim 4, wherein the server outputs a command for controlling the bed apparatus to the bed apparatus according to the bed information.

6. The remote watching system according to claim 4, wherein the bed apparatus includes:
    a frame;
    a bottom provided on the frame;
    an actuator capable of controlling a height of the frame and an angle of the bottom;
    casters attached to the frame; and
    side rails attached to the frame and configured to be openable and closable,
    wherein the bed information includes one or more types of information selected from a group including the height of the frame, the angle of the bottom, a locked state of the casters, and a locked state of the side rails.

7. The remote watching system according to claim 1, further comprising a mattress arranged on the bed apparatus, wherein the bed apparatus includes:
    a frame; and
    a bottom provided on the frame,
    wherein the sensor is arranged between the bottom and the mattress.

8. The remote watching system according to claim 1, wherein the biological information includes a heartbeat rate, respiratory rate, and body motion of the bed user.

9. The remote watching system according to claim 1, wherein the sensor determines whether the bed user is present on the bed apparatus based on the biological information.

10. The remote watching system according to claim 1, wherein the bed apparatus is operable by the mobile terminal.

11. A remote watching application installed on a mobile terminal capable of communicating with a server, the remote watching application receiving, from the server, a notification that is based on biological information about a bed user who uses a bed apparatus and issued from a sensor capable of communicating with the server and attached to the bed apparatus, and causing the mobile terminal to display a previously set notification,
- wherein the server automatically sets a notification to be output and a time period for which to output the notification, depending on an attribute of a user of the mobile terminal.

12. The remote watching application according to claim 11, wherein the notification is further based on bed information about the bed apparatus.

13. The remote watching application according to claim 11, wherein the remote watching application causes the mobile terminal to display the notification in such a way as to support a user of the mobile terminal to perform a determination.

\* \* \* \* \*